United States Patent
Ueyama

(10) Patent No.: US 10,001,533 B2
(45) Date of Patent: Jun. 19, 2018

(54) MAGNETIC PROPERTY DETERMINATION APPARATUS AND MAGNETIC PROPERTY DETERMINATION METHOD

(71) Applicant: GLORY LTD., Himeji-shi, Hyogo (JP)

(72) Inventor: Naoki Ueyama, Hyogo (JP)

(73) Assignee: GLORY LTD., Himeji-shi, Hyogo (JP)

( * ) Notice: Subject to any disclaimer, the term of this patent is extended or adjusted under 35 U.S.C. 154(b) by 0 days. days.

(21) Appl. No.: 15/125,982

(22) PCT Filed: Apr. 6, 2015

(86) PCT No.: PCT/JP2015/060707
§ 371 (c)(1),
(2) Date: Sep. 14, 2016

(87) PCT Pub. No.: WO2015/156241
PCT Pub. Date: Oct. 15, 2015

(65) Prior Publication Data
US 2017/0003358 A1  Jan. 5, 2017

(30) Foreign Application Priority Data

Apr. 9, 2014 (JP) ................................ 2014-080253

(51) Int. Cl.
*G01R 33/02* (2006.01)
*G01R 33/12* (2006.01)
(Continued)

(52) U.S. Cl.
CPC ............. *G01R 33/12* (2013.01); *G01N 27/72* (2013.01); *G01N 33/34* (2013.01);
(Continued)

(58) Field of Classification Search
CPC .. B64G 1/366; G01R 33/0206; G01R 33/028; G01R 33/038; G01R 33/1215;
(Continued)

(56) References Cited

U.S. PATENT DOCUMENTS

2008/0224806 A1* 9/2008 Ogden ................. H01F 13/003
335/284
2010/0327062 A1  12/2010 Lazzerini
(Continued)

FOREIGN PATENT DOCUMENTS

JP  3-248895 A  11/1991
JP  6-180304 A  6/1994
(Continued)

OTHER PUBLICATIONS

JPH06180304 machine translation, Jun. 28, 1994.*
WO 2010052797 machine translation, Mar. 29, 2012.*
European Search Report (Application No. 15777308.6) (14 pages—dated Jun. 11, 2017).

*Primary Examiner* — Huy Q Phan
*Assistant Examiner* — Raul Rios Russo
(74) *Attorney, Agent, or Firm* — Renner, Kenner, Greive, Bobak, Taylor & Weber

(57) ABSTRACT

A magnetic property determination apparatus that determines the magnetic materials on a paper sheet transported through a transport path includes a magnetization unit and a magnetic detection unit. The magnetization unit generates a magnetization magnetic field including a first magnetic field region and a second magnetic field region on the transport path. A magnetic field intensity and a magnetic field direction are set different between the first magnetic field region and the second magnetic field region so that the magnetic materials are magnetized in different magnetization directions depending on coercive forces of the magnetic materials. The magnetic detection unit that generates a bias magnetic field on the transport path downstream in a transport direction of the magnetization unit, and that detects a magnetic charge of the magnetic materials by detecting variations of the bias magnetic field.

7 Claims, 15 Drawing Sheets

(51) Int. Cl.
  *G01R 33/038* (2006.01)
  *G01R 33/028* (2006.01)
  *G07D 7/04* (2016.01)
  *G01N 27/72* (2006.01)
  *G01R 33/09* (2006.01)
  *G01N 33/34* (2006.01)

(52) U.S. Cl.
  CPC ....... *G01R 33/0206* (2013.01); *G01R 33/028* (2013.01); *G01R 33/038* (2013.01); *G01R 33/09* (2013.01); *G07D 7/04* (2013.01); *G01R 33/1215* (2013.01)

(58) Field of Classification Search
  CPC .... G01R 15/20; G01R 33/0283; G01R 33/38; G01N 27/90; G11C 19/085; H01F 7/0273
  USPC .................... 324/51, 55, 200, 227, 228, 244
  See application file for complete search history.

(56) References Cited

U.S. PATENT DOCUMENTS

| | | | |
|---|---|---|---|
| 2011/0233277 A1* | 9/2011 | Schutzmann | G07D 7/04 235/450 |
| 2013/0082105 A1* | 4/2013 | Schutzmann | G07D 7/04 235/450 |
| 2014/0028308 A1 | 1/2014 | Ogomi et al. | |
| 2014/0191035 A1* | 7/2014 | Paul | G07D 7/04 235/450 |
| 2015/0115947 A1* | 4/2015 | Yanagiuchi | G07D 7/04 324/244 |

FOREIGN PATENT DOCUMENTS

| WO | WO 2010/052797 A1 | 5/2010 |
|---|---|---|
| WO | WO 2014/168180 A1 | 10/2014 |

* cited by examiner

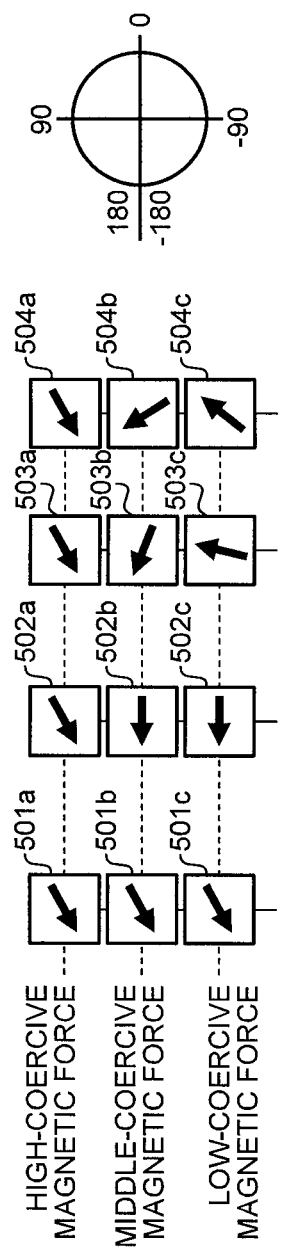
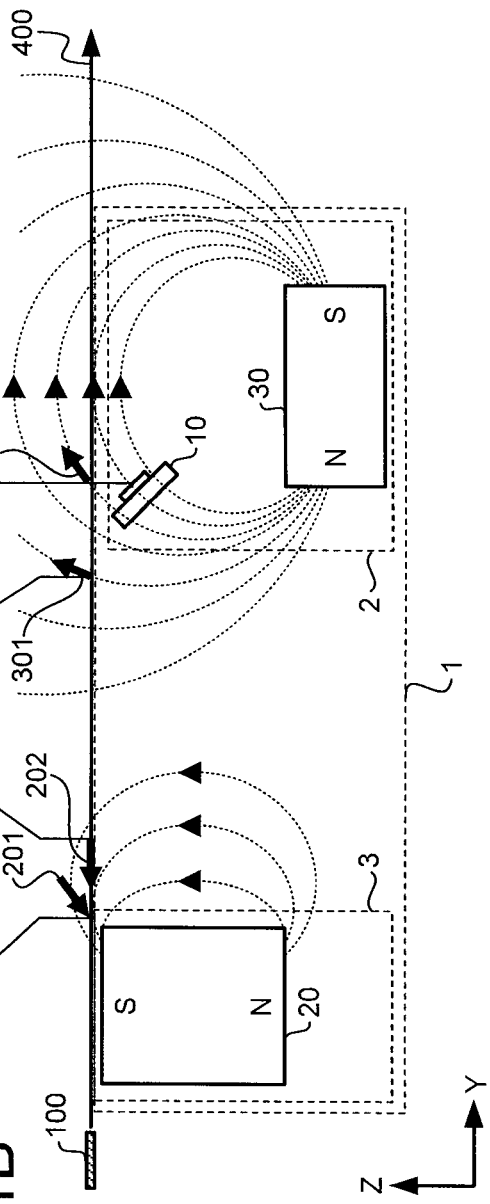

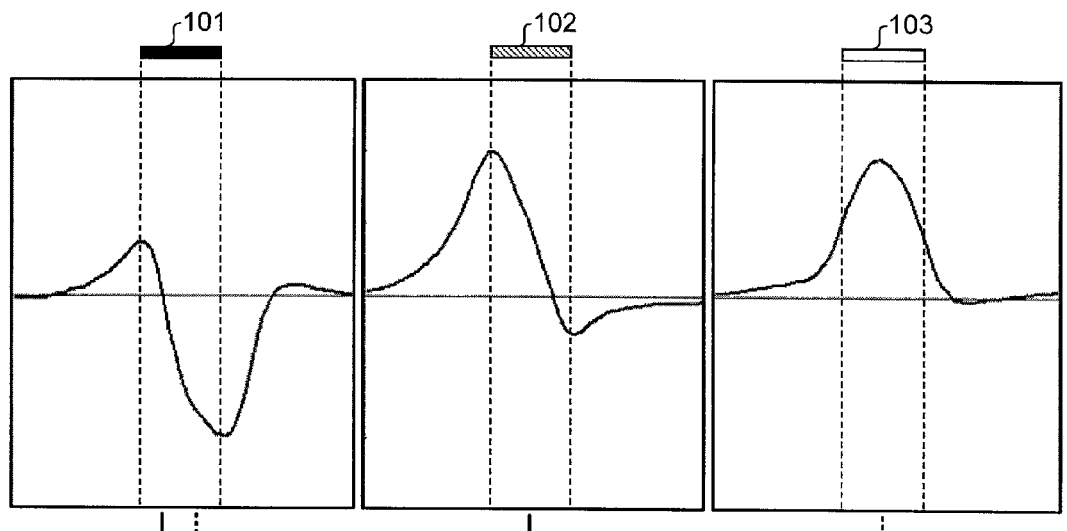
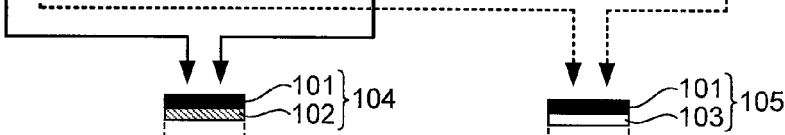
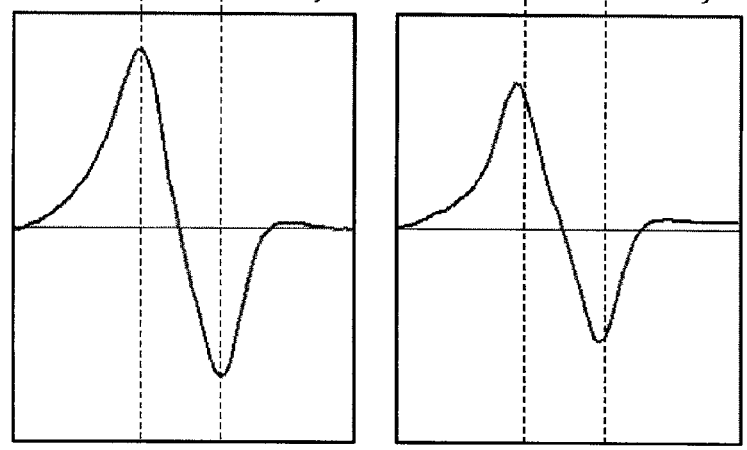

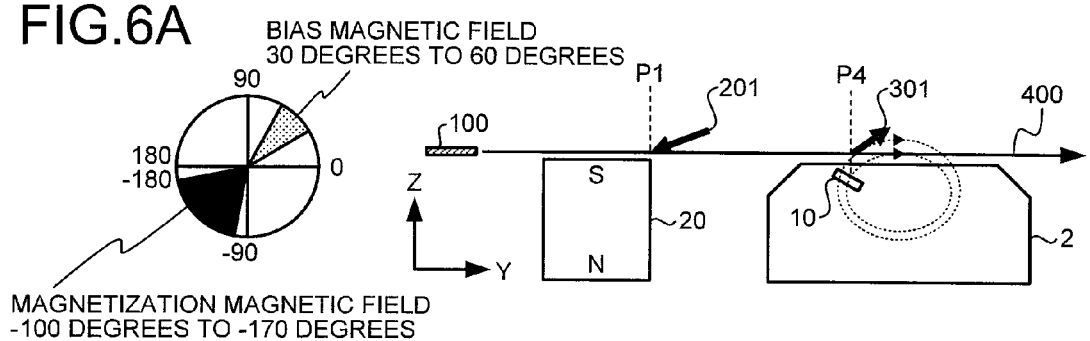
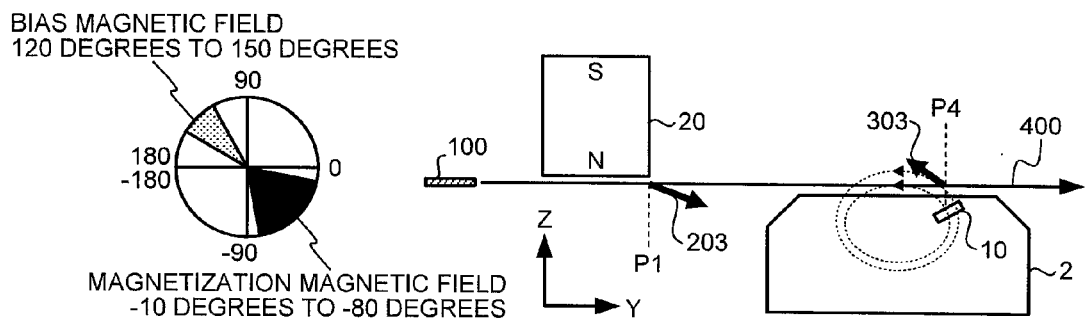
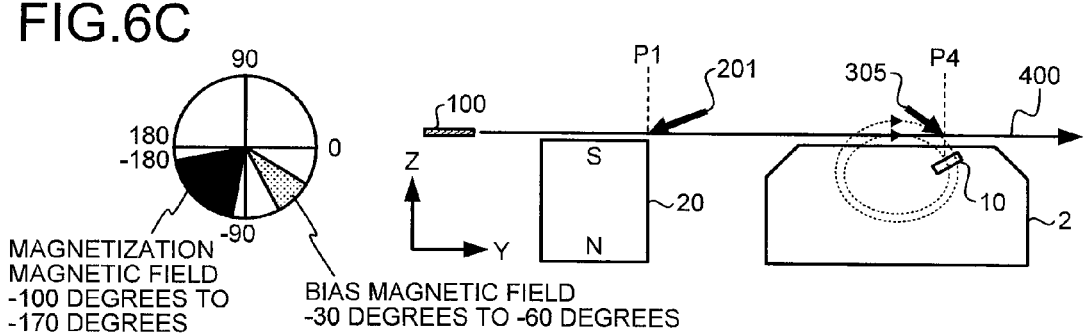
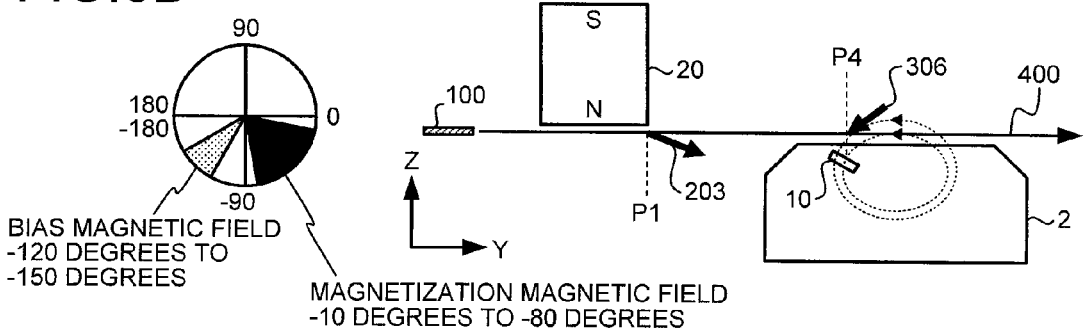

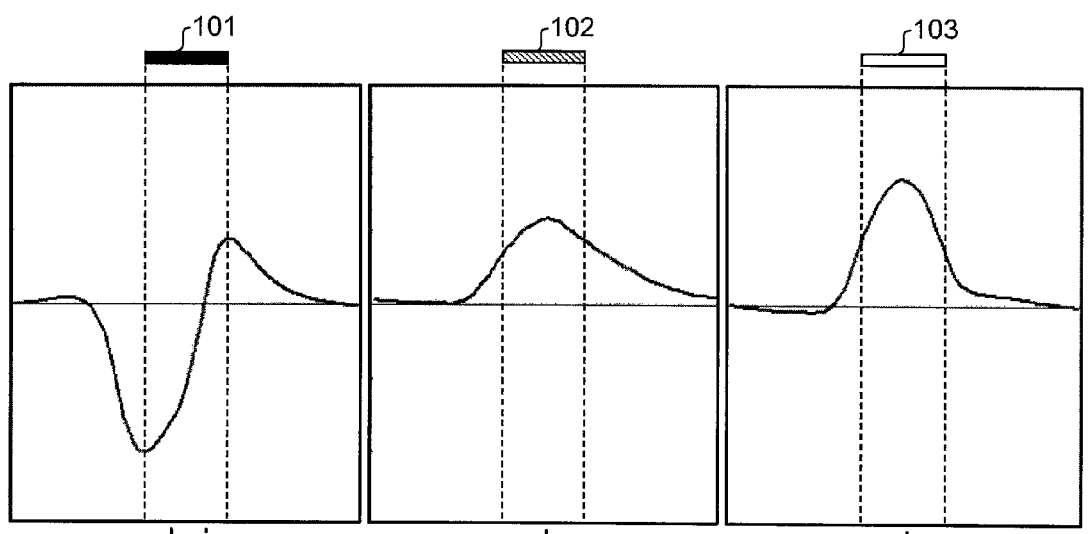
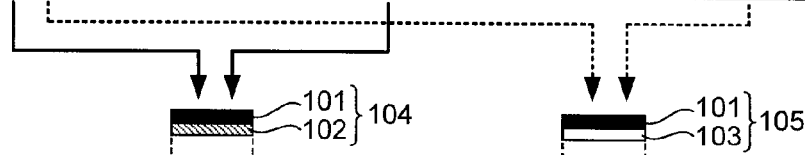
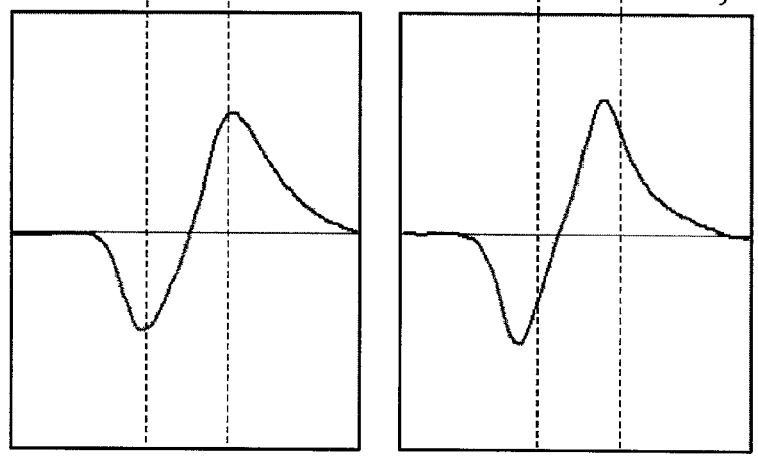
FIG.9D  FIG.9E

MAGNETIC PROPERTY DETERMINATION APPARATUS AND MAGNETIC PROPERTY DETERMINATION METHOD

TECHNICAL FIELD

The present invention generally relates to a magnetic property determination apparatus and a magnetic property determination method capable of detecting magnetism of a paper sheet. More specifically, the present invention specifically relates to a magnetic property determination apparatus and a magnetic property determination method capable of determining plural types of magnetic materials with different magnitudes of coercive force.

BACKGROUND ART

Conventionally, with an object to prevent forgery, magnetic ink including magnetic material has been used for printing on paper sheets such as checks, merchandise coupons, etc. Security techniques have been advancing year after year, and in recent years, there have been proposed paper sheets in which one paper sheet includes plural types of magnetic materials with different magnetic properties. For such paper sheets, it is necessary to determine each magnetic material included in the paper sheet to determine the authenticity of the paper sheet.

An example of an apparatus that determines plural types of magnetic materials included in a paper sheet has been disclosed in Patent Document 1. This document discloses an apparatus that determines magnetic materials with mutually different coercive forces. In this apparatus, a high-coercive force magnetic material and a low-coercive force magnetic material are magnetized in the same magnetization direction by a first magnet with a high magnetic force, and a detection signal corresponding to the magnetism of both the magnetic materials is obtained by using a first sensor. Subsequently, the magnetization direction of the low-coercive force magnetic material is changed by using a second magnet with a low magnetic force, and then a detection signal corresponding to the magnetism of the high-coercive force magnetic material only is obtained by using a second sensor. A difference between the detection signal obtained by the first sensor from both the high-coercive force magnetic material and the low-coercive force magnetic material and the detection signal obtained by the second sensor from only the high-coercive force magnetic material is taken as a detection signal obtained from only the low-coercive force magnetic material.

CITATION LIST

Patent Document

[Patent Document 1] U.S. Published Patent Application 2010/0327062

SUMMARY OF INVENTION

Technical Problem

However, in the conventional technique, because two magnets with a high magnetic force and a low magnetic force and two magnetic sensors are necessary, the number of parts increases, which leads to increase in the costs. Moreover, the overall structure becomes complicated and the size of the magnetic property determination apparatus increases.

The present invention has been devised to solve the problems explained above arising in the prior art. It is an object of the present invention to present a small-size magnetic property determination apparatus and a magnetic property determination method capable of determining plural types of magnetic materials with different magnitudes of coercive force.

Means for Solving Problems

To solve the above problem, and to achieve the above object, a magnetic property determination apparatus that detects a magnetic property of each magnetic material included in a paper sheet transported through a transport path and determines the magnetic materials according to one aspect of the present invention includes a magnetization unit that generates a magnetization magnetic field including a first magnetic field region and a second magnetic field region on the transport path, a magnetic field intensity and a magnetic field direction are set different between the first magnetic field region and the second magnetic field region so that the magnetic materials are magnetized in different magnetization directions depending on coercive forces of the magnetic materials, and a magnetic detection unit that generates a bias magnetic field on the transport path downstream than the magnetization unit in a transport direction, and that detects a magnetic charge of the magnetic materials by detecting variations of the bias magnetic field.

In the above magnetic property determination apparatus, the first magnetic field region, when the transport direction is 0 degree, is set in a range between −100 degrees and −170 degrees, and the magnetic field intensity thereof is set to 1.5 times or more of a coercive force of a high-coercive force magnetic material having the maximum coercive force among the magnetic materials to be determined.

In the above magnetic property determination apparatus, the second magnetic field region, when the transport direction is 0 degree, is set in a range between 100 degrees and 180 degrees, and the magnetic field intensity thereof is set to 1.5 times or more of a coercive force of a middle-coercive force magnetic material having a lower coercive force than the high-coercive force magnetic material and to 1 time or less of the coercive force of the high-coercive force magnetic material.

In the above magnetic property determination apparatus, the magnetization unit includes a magnet arranged above the transport path and another magnet arranged below the transport path.

In the above magnetic property determination apparatus, the magnetization unit further includes a magnetically permeable member arranged above the transport path and another magnetically permeable member arranged below the transport path.

In the above magnetic property determination apparatus, the first magnetic field region is generated by shifting in the transport direction the magnet arranged above the transport path and the another magnet arranged below the transport path, and the second magnetic field region is generated by shifting in the transport direction the magnetically permeable member arranged above the transport path and the magnetically permeable member arranged below the transport path.

In the above magnetic property determination apparatus, the magnetization unit has, in a surface facing toward the transport path, a first magnetic-pole surface substantially parallel to a transport surface and a second magnetic-pole surface that is distant from the transport surface than the first magnetic-pole surface.

In the above magnetic property determination apparatus, a magnetic field intensity between the first magnetic field region and the second magnetic field region is weaker than the magnetic field intensity of the first magnetic field region but stronger than the magnetic field intensity of the second magnetic field region, and a magnetic field intensity between the second magnetic field region and the bias magnetic field is weaker than the magnetic field intensity of the second magnetic field region.

In the above magnetic property determination apparatus, the first magnetic field region has a magnetic field intensity that magnetizes all types of coercive force magnetic materials, the magnetic field intensity between the first magnetic field region and the second magnetic field region is a magnetic field intensity that does not affect a magnetization direction of only the high-coercive force magnetic material, and the magnetic field intensity between the second magnetic field region and the bias magnetic field is a magnetic field intensity that does not affect the magnetization direction of the high-coercive force magnetic material, that affects a magnetization direction of the middle-coercive force magnetic material having a lower coercive force than the high-coercive force magnetic material, and that changes a magnetization direction of a low-coercive force magnetic material having a lower coercive force than the middle-coercive force magnetic material to the magnetic field direction thereof.

A magnetic property determination method of detecting a magnetic property of each magnetic material included in a paper sheet transported through a transport path and determining the magnetic materials according to another aspect of the present invention includes first generating a magnetization magnetic field including a first magnetic field region and a second magnetic field region on the transport path, a magnetic field intensity and a magnetic field direction are set different between the first magnetic field region and the second magnetic field region so that the magnetic materials are magnetized in different magnetization directions depending on coercive forces of the magnetic materials; and detecting a magnetic charge of the magnetic materials magnetized in the first generating by using a magnetic detection unit that generates a bias magnetic field on the transport path downstream in a transport direction than a magnetization position in the first generating, and that detects the magnetic charge of the magnetic materials by detecting variations of the bias magnetic field.

Advantageous Effects of Invention

According to the present invention, by using a magnetic charge detection type magnetic detection unit that generates a bias magnetic field in a magnetic field direction that is angled against a transport surface on which a paper sheet including a magnetic material is transported and detects the magnetism based on variation of the bias magnetic field, and a magnetization unit that magnetizes the magnetic material by using a magnetization magnetic field arranged on an upstream side in the transport direction and oriented in a direction different from the direction of the bias magnetic field, and in detecting magnetism by the magnetic detection unit, the magnetic materials have been magnetized in mutually different magnetization directions based on their coercive force, and thus the magnetic materials can be differentiated and determined based on detection waveforms that are different according to the coercive force of the respective magnetic material.

BRIEF DESCRIPTION OF DRAWINGS

FIGS. 1A and 1B are views that show a magnetic property determination method performed by a magnetic property determination apparatus according to a first embodiment.

FIGS. 5A, 5B, 5C, 5D, and 5E are views that show magnetic material detection signals obtained by the magnetic property determination apparatus.

FIGS. 6A, 6B, 6C, and 6D are views that show magnetic property determination apparatuses with a direction of a magnetization magnetic field being different from a direction of a bias magnetic field.

FIGS. 9A, 9B, 9C, 9D, and 9E are views that show a magnetism detection signal obtained by the magnetic property determination apparatus that transports the paper sheet in the reverse direction.

DESCRIPTION OF EMBODIMENTS

Figure 2:
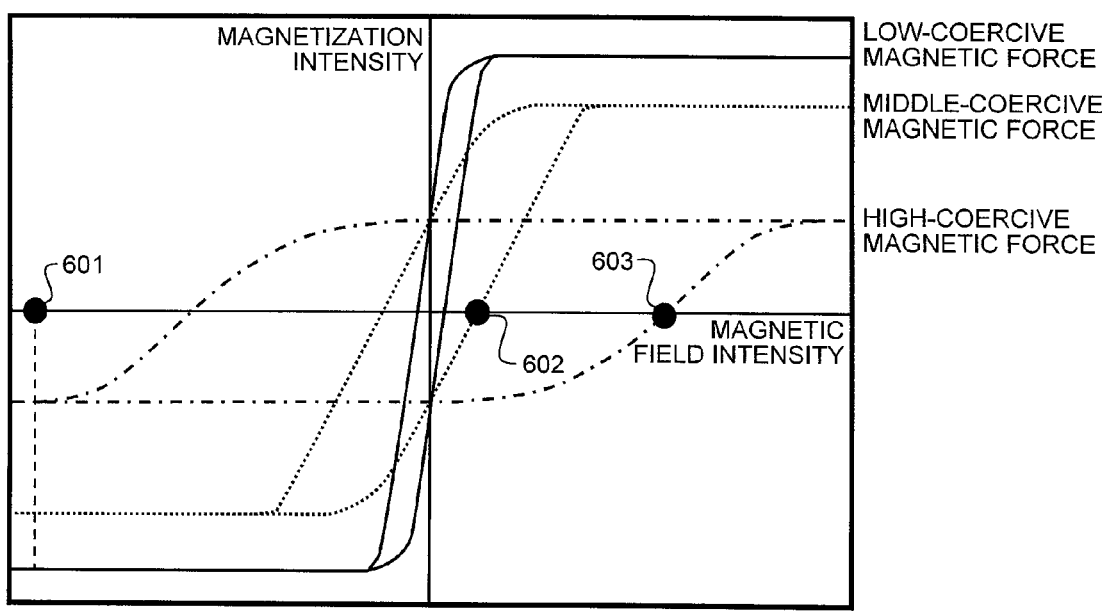
FIG. 2 is a view that shows magnetic field intensity of a magnetization magnetic field and a bias magnetic field.

Exemplary embodiments of a magnetic property determination apparatus and a magnetic property determination method according to the present invention are explained in detail below with reference to the accompanying drawings. The magnetic property determination apparatus according to the present embodiment detects magnetism of various magnetic materials used to perform printing on paper sheets such as checks, merchandise coupons, and valuable securities and determines the type of the magnetic material. The magnetic property determination apparatus is used in a paper sheet treatment apparatus to determine whether a paper sheet is authentic or not by determining the type of the magnetic material included in the paper sheet, for example.

The magnetic property determination apparatus according to the present embodiment is capable of determining which of a high-coercive force magnetic material, a middle-coercive force magnetic material, and a low-coercive force magnetic material the magnetic material is based on a detection signal obtained from the magnetic material. Magnetic materials that can be determined are a high-coercive force magnetic material, a middle-coercive force magnetic material, and a low-coercive force magnetic material in descending order of the coercive force. The terms "high-coercive force magnetic material", "middle-coercive force magnetic material", and "low-coercive force magnetic material" refer to magnetic materials in which the ratio of coercive force of the high-coercive force magnetic material to coercive force of the middle-coercive force magnetic material is 2 times or more and the ratio of coercive force of the middle-coercive force magnetic material to coercive force of the low-coercive force magnetic material is 2 times or more. It is desirable that these ratios of the coercive forces are as high as possible but preferably 2 times or more. Specifically, in determination performed by a magnetic property determination apparatus 1, a magnetic material of coercive force of 50 Oe is determined as a low-coercive force magnetic material, a magnetic material of coercive force of 300 Oe is determined as a middle-coercive force magnetic material, and a magnetic material of coercive force of 3,000 Oe is determined as a high-coercive force magnetic material, for example. The respective magnetic materials of the above-mentioned magnitudes of coercive force will be referred to as a "low-coercive force magnetic material", a "middle-coercive force magnetic material", and a "high-coercive force magnetic material", respectively.

First Embodiment

FIG. 1 is a schematic diagram for explaining a magnetic property determination method performed by the magnetic property determination apparatus 1 according to the present embodiment. FIG. 1B shows an outline of the magnetic property determination apparatus 1 and FIG. 1A shows the magnetized states of 3 types of magnetic materials with mutually different coercive forces.

Referring to FIG. 1B, the magnetic property determination apparatus 1 includes a magnetization unit 3 that magnetizes a magnetic material included in a paper sheet 100 transported on an upper portion of the apparatus, and a magnetic detection unit 2 that detects magnetism of the magnetic material included in the paper sheet 100.

The paper sheet 100 is transported by a not-shown transport mechanism over a transport path in a direction of an arrow 400 shown in FIG. 1B. The magnetic property determination apparatus 1 is arranged below the transport path. In the magnetic property determination apparatus 1, the magnetization unit 3 is arranged upstream of the magnetic detection unit 2 in the direction of transport. The magnetic material included in the paper sheet 100 is magnetized when the paper sheet 100 passes above the magnetization unit 3. Subsequently, a signal is obtained from the magnetic material when the paper sheet 100 is further transported and passes on the magnetic detection unit 2. The type of the magnetic material is determined based on the obtained detection signal.

The magnetization unit 3 includes a magnetization magnet 20 that generates a magnetization magnetic field that is oriented in a direction shown in FIG. 1B by broken line arrows. The magnetization magnetic field has magnetic field intensity that can magnetize all the magnetic materials that are targets of determination into a saturation magnetization state. Specifically, in order to magnetize the high-coercive force magnetic material having the highest coercive force among the magnetic materials that are targets of determination into the saturation magnetization state, the magnetic field intensity of the magnetization magnetic field shall be 1.5 times or more than the coercive force of the high-coercive force magnetic material. However, in order to obtain a complete saturation magnetization state, it is preferable that the magnetic field intensity of the magnetization magnetic field is 3 times or more than the coercive force of the high-coercive force magnetic material.

At the time of detecting the magnetic material, if the magnetic materials with mutually different coercive forces can be magnetized in mutually different magnetization directions, it is not necessary to magnetize the high-coercive force magnetic material into a complete saturation magnetization state. That is, it is sufficient that the high-coercive force magnetic material is magnetized into a state that is close to the saturation magnetization state. This will be explained in more detail below.

The magnetic detection unit 2 includes a bias magnet 30 that generates a bias magnetic field and a magnetic sensor 10 that detects magnetic material passing through the bias magnetic field and outputs a signal representing detection of the magnetic material. The bias magnet 30 generates a bias magnetic field around it in a manner shown in FIG. 1B by broken line arrows. One characteristic feature of the magnetic detection unit 2 is that the magnetic sensor 10 is arranged in an inclined state so as to make an angle with respect to a transport surface (X-Y plane) on which the paper sheet 100 is transported. With this configuration, a detection signal that corresponds to the magnetic charge of the magnetic material is outputted from the magnetic sensor 10. In the present embodiment, an example in which the magnetic sensor 10 includes one magnetic detection element is explained; however, the magnetic sensor 10 can include two magnetic detection elements. The magnetic sensor 10 is operative to detect the amount of variation of the bias magnetic field that fluctuates in the vertical direction in FIG. 1B when magnetic material passes by. For example, a magneto-resistive element is used as the magnetic detection element, variation of the value of resistance of the magneto-resistive element is outputted as variation of the voltage value, and the voltage value is used as a detection signal obtained from the magnetic material. Details of the configuration, functions, and operations of the magnetic charge detection type magnetic detection unit 2 will be omitted herefrom because, for example, Japanese Patent No. 4894040 discloses such configuration, functions, and operations.

Similarly to the magnetic field intensity of the magnetization magnetic field, the magnetic field intensity of the bias magnetic field generated by the magnetic detection unit 2 is set according to the coercive force of the magnetic material that is the target of determination. FIG. 2 schematically shows saturation magnetization curves (B-H curves) for the 3 types of magnetic materials that are targets of determination by the magnetic property determination apparatus 1, i.e., the low-coercive force magnetic material, the middle-coercive force magnetic material, and the high-coercive force magnetic material. The magnetic field intensity of the bias magnetic field is set to a magnitude between a coercive force 602 of middle-coercive force magnetic material and a coercive force 603 of high-coercive force magnetic material so that the low-coercive force magnetic material is magnetized into the saturation magnetization state while the middle-coercive force magnetic material is not magnetized into the saturation magnetization state. Specifically, the magnetic field intensity of the bias magnetic field is set, for example, 1.5 times of the coercive force 602 of middle-coercive force magnetic material. The magnetic field intensity of the magnetization magnetic field generated by the magnetization unit 3 corresponds to a point 601 shown in FIG. 2.

Next, a method for determining the magnetic materials including the high-coercive force magnetic material, the middle-coercive force magnetic material, and the low-coercive force magnetic material performed by the magnetic property determination apparatus 1 shown in FIG. 1B will be explained. In the following explanation, the direction of the magnetic field will be represented by using arrows and angles as shown in the drawing. With regard to the angles, as shown in the right portion of FIG. 1A, the positive side of the Y-axis, which is same as the transport direction 400, is taken as 0 degree, the positive side of the Z-axis, which extends above and orthogonal to the transport path, is taken as 90 degrees, and the negative side of the Y-axis, which extends opposite to the transport direction 400, is taken as 180 degrees. Similarly, the positive side of the Y-axis that is taken as 0 degree, the negative side of the Z-axis, which extends below and orthogonal to the transport path, is taken as −90 degrees, and the negative side of the Y-axis is taken as −180 degrees.

It is assumed that, for example, the magnetic field intensity of the magnetization magnetic field generated by the magnetization unit 3 shall be 1.5 times (4,500 G) of the coercive force of the high-coercive force magnetic material (3,000 Oe) at a position P1 on the transport path corresponding to an edge of the magnetization magnet 20 shown in FIG. 1B on the side of the south (S) pole thereof and on the side of the transport path. Moreover, for example, the magnetic field intensity of the bias magnetic field in the magnetic detection unit 2 is 1.5 times (450 G) than the coercive force (300 Oe) of the middle-coercive force magnetic material at a position P4 on the transport path at which the magnetism of the respective magnetic material is detected by the magnetic sensor 10.

At the position P4 at which the magnetism of the magnetic material is detected by the magnetic sensor 10, a direction 302 of the bias magnetic field is set between 30 degrees and 60 degrees. A direction 201 of the magnetization magnetic field at the position P1 is set based on the coercive force of the magnetic material that is the target of determination; however, if a high-coercive force magnetic material is the target of determination, the magnetic field direction 201 is set within a range between −100 degrees and −170 degrees. In the following description, it is assumed that the magnetic field direction at the position P1 is −160 degrees.

If the magnetic material included in the paper sheet 100 is the high-coercive force magnetic material (of 3,000 Oe), when the paper sheet 100 is transported on the magnetization unit 3 in the transport direction 400, the magnetic material is magnetized to the saturation magnetization state or to a state close to the saturation magnetization state when the magnetic material passes the position P1 shown in FIG. 1B because the magnetic field intensity of the magnetization magnetic field is very high (4,500 G). In this process, as shown in FIG. 1A, a magnetization direction 501a of the high-coercive force magnetic material is the same direction (about −160 degrees) as the direction 201 of the magnetization magnetic field at the position P1. The high-coercive force magnetic material attains the saturation magnetization state when its magnetization direction is between −150 degrees and −170 degrees.

As the paper sheet 100 passes the position P1 shown in FIG. 1B and is further transported in the transport direction 400, the intensity of the magnetization magnetic field steadily decreases, and thus the paper sheet 100 is not affected by the magnetization magnetic field. Accordingly, the magnetized state of the high-coercive force magnetic material does not change and a magnetization direction 502a of the high-coercive force magnetic material when the paper sheet 100 passes a position P2 remains to be in the same direction as that of the magnetization direction 501a at the magnetization position P1.

Even when the paper sheet 100 is further transported and enters the bias magnetic field, the paper sheet 100 is not influenced by the bias magnetic field, because, the intensity (450 G) of the bias magnetic field is ⅙ or less of the coercive force of the high-coercive force magnetic material (3,000 Oe). Accordingly, a magnetization direction 503a when the magnetic material passes a position P3 and a magnetization direction 504a when the magnetic material passes the position P4 also remain to be the same direction as that of the magnetization direction 501a (about −160 degrees) that is the magnetization direction at the time of the magnetization.

If the magnetic material included in the paper sheet 100 is the middle-coercive force magnetic material, as shown in FIG. 1B, similar to the case of the high-coercive force magnetic material, when the paper sheet 100 is transported on the magnetization unit 3 in the transport direction 400, the magnetic material is magnetized into the saturation magnetization state at the position P1. In this process, similar to the case of the high-coercive force magnetic material, a magnetization direction 501b of the middle-coercive force magnetic material is the same direction as the direction 201 of the magnetization magnetic field at the position P1. However, in the case of the middle-coercive force magnetic material, because the coercive force of the middle-coercive force magnetic material is lower than that of the high-coercive force magnetic material, the paper sheet 100 is continuously influenced by the magnetization magnetic field while the paper sheet 100 is transported in the transport direction 400, and thus its magnetization direction varies according to the direction of the magnetization magnetic field. When the paper sheet 100 passes the position P2, a magnetization direction 502b of the middle-coercive force magnetic material becomes the same direction as a direction 202 of the magnetization magnetic field (about 180 degrees). When the paper sheet 100 is further transported, the magnetic field intensity decreases while the direction of the magnetization magnetic field changes from the direction of 180 degrees to the direction of 170 degrees, and the action of magnetization of the middle-coercive force magnetic material is lost.

When the paper sheet 100 is further transported and enters the bias magnetic field, the paper sheet 100 is influenced by the bias magnetic field. At the position P3, the magnetization direction is shifted toward the same direction as a direction 301 of the bias magnetic field at the position P3 to a magnetization direction 503b that is a direction slightly rotated from the magnetization direction 502b at the position P2. Moreover, the magnetization direction is rotated toward the same direction as the bias magnetic field direction 302 at the position P4 to a magnetization direction 504*b* that is a direction slightly rotated from the magnetization direction 503*b* at the position P3. However, the intensity (450 G) of the bias magnetic field is lower than the magnetic field intensity for turning the coercive force of the middle-coercive force magnetic material into the saturation magnetization state (300 Oe). Accordingly, a final magnetization direction of the middle-coercive force magnetic material is the magnetization direction 504*b*, which is a direction between the magnetization direction 502*b* that is the magnetization direction when the paper sheet 100 exits the magnetization magnetic field (about 180 degrees) and the direction 302 of the bias magnetic field at the position P4 (between 30 degrees and 60 degrees). For example, the magnetization direction 504*b* of the middle-coercive force magnetic material at the position P4 is about 120 degrees.

If the magnetic material included in the paper sheet 100 is the low-coercive force magnetic material, similarly to the cases of other magnetic materials, when the paper sheet 100 is transported on the magnetization unit 3 in the transport direction 400, as shown in FIG. 1B, the magnetic material is magnetized into the saturation magnetization state at the magnetizing position P1. In this process, similarly to the cases of other magnetic materials, a magnetization direction 501*c* of the low-coercive force magnetic material is the same direction as the direction 201 of the magnetization magnetic field at the magnetizing position P1. However, the coercive force of the low-coercive force magnetic material is low. Accordingly, the paper sheet 100 is continuously influenced by the magnetization magnetic field while the paper sheet 100 is transported in the transport direction 400, and the magnetization direction varies according to the direction of the magnetization magnetic field. Accordingly, similarly to the case of the middle-coercive force magnetic material, a magnetization direction 502*c* when the paper sheet 100 passes the position P2 is the same direction as the direction 202 of the magnetization magnetic field (about 180 degrees).

When the paper sheet 100 is further transported and enters the bias magnetic field, the low-coercive force magnetic material is also influenced by the bias magnetic field. At the position P3, the magnetization direction 502*c* of the low-coercive force magnetic material is a magnetization direction 503*c* that is the same as the direction 301 of the bias magnetic field at the position P3. At the position P4 also, the magnetization direction of the low-coercive force magnetic material is a magnetization direction 504*c* that is the same magnetization direction as the direction 302 of the bias magnetic field. Because the magnetic field intensity of the bias magnetic field (450 G) is sufficiently higher than the coercive force of the low-coercive force magnetic material (50 Oe) and the low-coercive force magnetic material turns into the saturation magnetization state at the respective positions, the magnetization direction of the low-coercive force magnetic material at the each of the above-mentioned positions is the direction that is the same as the direction of the bias magnetic field at those positions.

It is said that the magnetic field intensity that is 3 times higher than the coercive force is required to turn the magnetic material into the saturation magnetization state. Accordingly, in the magnetic property determination apparatus 1, the intensity of the bias magnetic field at the position P4 at which magnetism is detected by the magnetic sensor 10 is set 3 times or more than the low-coercive force magnetic material that is the target of determination and 2 times or less than the coercive force of the middle-coercive force magnetic material. However, this does not apply around the magnetic field with the magnetic field intensity equivalent to the coercive force of the middle-coercive force magnetic material. The reason is because the output of the magnetic material of the middle-coercive force magnetic material becomes 0 in the bias magnetic field. For example, the magnetic field intensity is set to 450 Oe so that the middle-coercive force magnetic material of the coercive force of 300 Oe would not be magnetized into the saturation magnetization state but the low-coercive force magnetic material of the coercive force of 50 Oe is turned into the saturation magnetization state. The magnetization direction 504*c* at the position P4 of the low-coercive force magnetic material can be thereby set to the same direction as the bias magnetic field direction 302 at the position P4. On the contrary, the magnetization magnetic field is set so that the magnetization direction of the middle-coercive force magnetic material varies in the bias magnetic field but it would be oriented in a direction that is not the same as the bias magnetic field direction 302 after the magnetization direction of the middle-coercive force magnetic material has varied. Accordingly, the magnetization direction 504*b* of the middle-coercive force magnetic material at the position P4 and the magnetization direction 504*c* of the low-coercive force magnetic material can be set to be mutually different.

In the case of the high-coercive force magnetic material, the magnetization direction remains to be in the magnetization direction 501*a* that is the same direction as the direction 201 of the magnetization magnetic field without being influenced by the bias magnetic field. However, because the direction 201 of the magnetization magnetic field has been set so as to be different from the magnetization direction 504*b* of the middle-coercive force magnetic material at the position P4 and the magnetization direction 504*c* of the low-coercive force magnetic material at the position P4, the magnetization direction 504*a* of the high-coercive force magnetic material at the position P4 can be set to a direction different from the magnetization directions 504*b* and 504*c* of other magnetic materials. If the magnetization direction 504*a* of the high-coercive force magnetic material can be set to a direction different from the magnetization directions 504*b* and 504*c* of the middle-coercive force magnetic material and the low-coercive force magnetic material, it is not necessary to magnetize the high-coercive force magnetic material into the saturation magnetization state, and it is allowable that the high-coercive force magnetic material is magnetized into a state close to the saturation magnetization state.

As explained above, one of the characteristics of the present invention is that, in the magnetic property determination apparatus 1, at the position P4 where the magnetic detection unit 2 detects the magnetism in the transport path, all of the magnetization direction 504*a* of the high-coercive force magnetic material, the magnetization direction 504*b* of the middle-coercive force magnetic material, and the magnetization direction 504*c* of the low-coercive force magnetic material are oriented in different directions.

In the magnetic property determination apparatus 1 shown in FIG. 1, the magnetic field intensity of the magnetization magnetic field generated by the magnetization unit 3 is set to the magnetic field intensity with which the high-coercive force magnetic material can be magnetized into the saturation magnetization state and the magnetic field intensity of the bias magnetic field is set to the magnetic field intensity that does not influence the magnetized state of the high-coercive force magnetic material. Moreover, the direction 201 of the magnetization magnetic field at the position P1 at which the high-coercive force magnetic material is magnetized into the saturation magnetization state and the direction 302 of the bias magnetic field at the position P4 at which the magnetic material is detected are set so as to fall in the quadrants that are mutually opposite with respect to the origin. Furthermore, the intensity of the bias magnetic field at the position P4 is set to intensity for magnetizing the low-coercive force magnetic material into the saturation magnetization state and not magnetizing the middle-coercive force magnetic material into the saturation magnetization state. By performing the setting in the above-explained manner, at the position P4, the magnetization direction 504a of the high-coercive force magnetic material can be set to the same direction as the direction 201 of the magnetization magnetic field, the magnetization direction 504c of the low-coercive force magnetic material can be set to the same direction as the direction 302 of the bias magnetic field, and the magnetization direction 504b of the middle-coercive force magnetic material can be set to a direction between the magnetization direction 504a of the high-coercive force magnetic material and the magnetization direction 504c of the low-coercive force magnetic material. If the magnetization directions and the magnetic field intensities of the magnetization magnetic fields explained above can be achieved, the type, the number, the shape, and the like of the magnetization magnet 20 of the magnetization unit 3 are not particularly limited.

Next, detection signals acquired when the high-coercive force magnetic material, the middle-coercive force magnetic material, and the low-coercive force magnetic material having been magnetized into the magnetization directions different from one another as explained above are detected by the magnetic sensor 10 of the magnetic detection unit 2 will be explained.

FIG. 3 shows magnetic field distributions in the Z-axis direction at locations close to a location immediately below the magnetic material having been magnetized into magnetization directions 507 to 510 (at a location about 0.5 mm below the magnetic material). The magnetic field distribution in the Z-axis direction is shown in FIG. 3A when the magnetization direction is in the upward magnetization direction 507. The magnetic field distribution in the Z-axis direction is shown in FIG. 3B when the magnetization direction is in the leftward direction 508. The magnetic field distributions in the Z-axis direction are shown in FIG. 3C and FIG. 3D when the magnetization directions are the inclined directions 509 and 510. When a magnetic material that has been magnetized passes through the bias magnetic field generated by the bias magnet 30, the direction and the density of the bias magnetic field vary as shown in FIG. 3. The magnetic sensor 10 outputs the variation of the bias magnetic field as a detection signal. The leftward direction in FIG. 3 corresponds to the direction of 180 degrees in FIG. 1 and the upward direction in FIG. 3 corresponds to the direction of 90 degrees in FIG. 1.

Figure 4A:
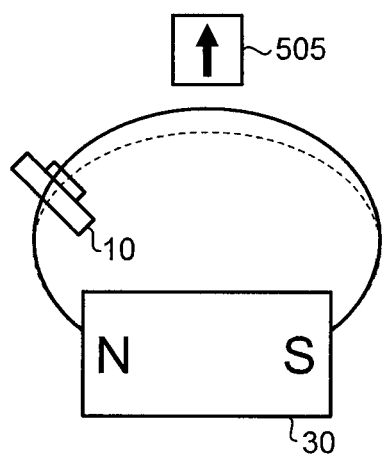
FIGS. 4A and 4B are views that show a relationship between the magnetized state and the detection signal obtained by a magnetic sensor.
Figure 4B:
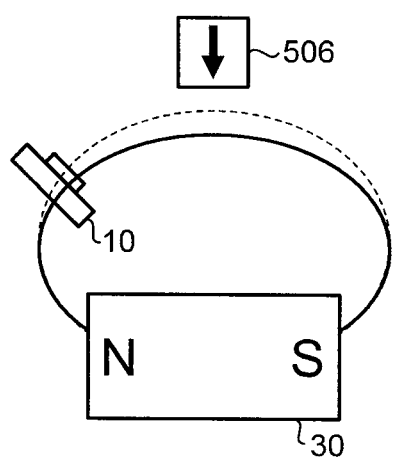

FIG. 4A and FIG. 4B are views that show a relationship between variation of the bias magnetic field and the detection signal from the magnetic sensor 10. In FIG. 4A and FIG. 4B, the magnetization direction of the magnetic material that passes through the bias magnetic field is shown in the upper portion, and the variation of the magnetic lines of force of the bias magnetic field is illustrated in the lower portion. As shown in FIG. 4A, when a magnetic material with a magnetization direction 505 passes the position P4 at which the magnetic sensor 10 detects the magnetic material, the magnetic line of force shifts upwardly as indicated by a solid line from an initial state indicated by a broken line. A setting has been performed so that a positive output detection signal can be obtained at the magnetic sensor 10 in response to the variation of the direction of the bias magnetic field and the variation of the magnetic flux density thereof. On the contrary, as shown in FIG. 4B, when a magnetic material with a magnetization direction 506 passes the position P4 at which the magnetic sensor 10 detects the magnetic material, the magnetic line of force shifts downwardly as indicated by a solid line from an initial state indicated by a broken line. In this case, a setting has been performed so that a negative output detection signal can be obtained at the magnetic sensor 10 in response to the variation of the direction of the bias magnetic field and the variation of the magnetic flux density thereof.

FIG. 5A to FIG. 5E show waveforms of the detection signals acquired in the magnetic property determination apparatus 1 as shown in FIG. 1B when the magnetic detection unit 2 detects a high-coercive force magnetic material 101, a middle-coercive force magnetic material 102, a low-coercive force magnetic material 103, and laminated magnetic materials 104 and 105. Outputs from the magnetic sensor 10 are taken on the ordinate axis and time is taken on the abscissa axis. When the paper sheet 100, which includes the respective magnetic material, passes the position P4, the detection signals outputted from the magnetic sensor 10 has the waveforms shown in FIG. 5A to FIG. 5E. The respective magnetic materials 101 to 105 corresponding to the respective detection signals are shown in the upper portions of FIG. 5A to FIG. 5E.

In the case of the low-coercive force magnetic material 103 shown in FIG. 5C, a positive output is obtained in substantially the entire range, and the waveform is substantially symmetrical across the peak position. Because the low-coercive force magnetic material 103 is in a state in which it is saturation-magnetized by the bias magnetic field, the waveform of the detection signal outputted from the magnetic sensor 10 is not a waveform generated by the magnetic field generated by the low-coercive force magnetic material. Because the low-coercive force magnetic material has a high magnetic permeability and acts to converge the magnetic lines of force, the amplitude of the detection signal outputted from the magnetic sensor 10 increases as the low-coercive force magnetic material comes close to the position P4. Accordingly, the detection signal obtained when the low-coercive force magnetic material is detected has a maximum value when the magnetic material passes a location near the position P4 and takes substantially symmetrical waveform across the maximum value. For the middle-coercive force magnetic material and the high-coercive force magnetic material, the generated magnetic field is asymmetric for the magnetic field other than the upward direction (between 80 degrees and 100 degrees), and thus the detection signal necessarily becomes asymmetric across the maximum value.

Figure 3A:
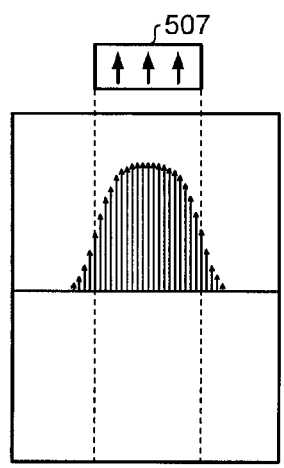
FIGS. 3A, 3B, 3C, and 3D are views that show a magnetized state when magnetism is detected from a magnetic material.
Figure 3B:
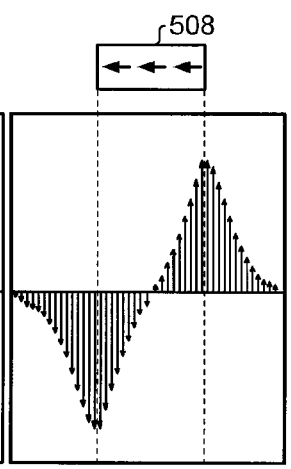
Figure 3C:
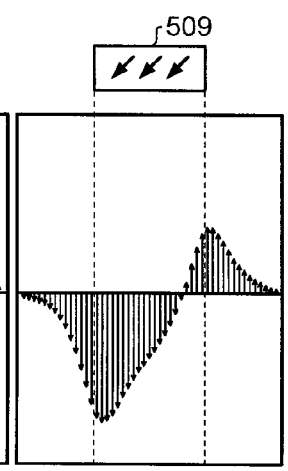
Figure 3D:
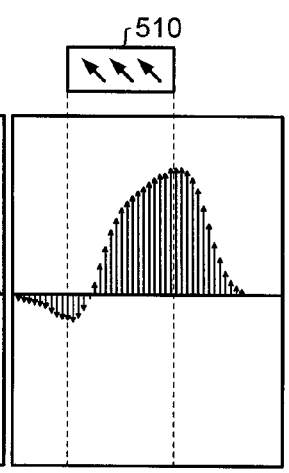

FIG. 5B shows a detection signal obtained from the middle-coercive force magnetic material 102. At the position P4 in the magnetic property determination apparatus 1 shown in FIG. 1B, the magnetization direction of the middle-coercive force magnetic material is oriented in the upward left direction. The magnetic field distribution immediately below and near the middle-coercive force magnetic material in the Z-axis direction in this case is as shown in FIG. 3D, and a magnetic signal is detected so as to go along the shape of the magnetic field distribution from the right. As a result, as shown in FIG. 5B, the detection signal changes from a positive output to a negative output. As explained above, the portion of the detection signal having the positive output is larger for the middle-coercive force magnetic material 102. Similarly to the case of the low-coercive force magnetic material 103, the output of the detection signal of the middle-coercive force magnetic material 102 is positive for the substantially entire range; however, because the waveform of a positive output is asymmetric across the peak position, the detection signal of the middle-coercive force magnetic material 102 can be differentiated from the detection signal of the low-coercive force magnetic material 103.

FIG. 5A shows a detection signal obtained from the high-coercive force magnetic material 101. At the position P4 in the magnetic property determination apparatus 1 shown in FIG. 1B, the magnetization direction of the high-coercive force magnetic material is oriented in the downward left direction. The magnetic field distribution at a position close to a position immediately below the high-coercive force magnetic material in the Z-axis direction at this timing is as shown in FIG. 3C, and a magnetic signal is detected so as to go along the shape of the magnetic field distribution from the right. As a result, as shown in FIG. 5A, the detection signal changes from a positive output to a negative output. In the case of the high-coercive force magnetic material 101, the positive output takes an asymmetric waveform similar to the case of the middle-coercive force magnetic material 102; however, because the portion of the negative output is higher compared with the detection signal of the middle-coercive force magnetic material 102 shown in FIG. 5B, the detection signal of the high-coercive force magnetic material 101 can be differentiated from the detection signal of the low-coercive force magnetic material 103 and the detection signal of the middle-coercive force magnetic material 102.

For the laminated magnetic material 104 shown in FIG. 5D and constituted by the high-coercive force magnetic material 101 and the middle-coercive force magnetic material 102, the detection signal changes from a positive output to a negative output. The waveform of the detection signal obtained from of the laminated magnetic material 104 is obtained by adding the detection signal of the high-coercive force magnetic material 101 and the detection signal of the middle-coercive force magnetic material 102. The detection signal obtained from the laminated magnetic material 104 has both positive and negative outputs similarly to the high-coercive force magnetic material 101 shown in FIG. 5A. However, differently from the detection signal of the high-coercive force magnetic material 101, the amplitude is substantially the same for the positive output and the negative output in the detection signal of the laminated magnetic material 104, and thus the detection signal of the laminated magnetic material 104 and the detection signal of the high-coercive force magnetic material 101 can be differentiated from each other. If only one type of laminated magnetic material is included in the magnetic material that is the target of determination and the laminated magnetic material is the laminated magnetic material 104 including the high-coercive force magnetic material 101 and the middle-coercive force magnetic material 102, it can be recognized by using the above-explained determination method that the laminated magnetic material 104 exists at a specific location on the paper sheet 100.

In case of the laminated magnetic material 105 shown in FIG. 5E constituted by the high-coercive force magnetic material 101 and the low-coercive force magnetic material 103, the detection signal changes from a positive output to a negative output. The waveform of the detection signal obtained from the laminated magnetic material 105 is obtained by adding the detection signal of the high-coercive force magnetic material 101 and the detection signal of the low-coercive force magnetic material 103. The detection signal of the laminated magnetic material 105 has both positive and negative outputs similarly to the detection signal obtained from the high-coercive force magnetic material 101 shown in FIG. 5A. However, differently from the detection signal obtained from the high-coercive force magnetic material 101, the amplitude is substantially the same for the positive output and the negative output in the detection signal obtained from the laminated magnetic material 105. Accordingly, the detection signal obtained from the laminated magnetic material 105 and the detection signal obtained from the high-coercive force magnetic material 101 can be differentiated from each other. If only one type of laminated magnetic material is included in the target object of determination and the laminated magnetic material is the laminated magnetic material 105 including the high-coercive force magnetic material 101 and the low-coercive force magnetic material 103, it can be recognized by using the above-explained determination method that the laminated magnetic material 105 exists at a specific location on the paper sheet 100.

In the method of determining the laminated magnetic material, except for a case in which both of a combination of the high-coercive force magnetic material 101 and the middle-coercive force magnetic material 102 and a combination of the high-coercive force magnetic material 101 and the low-coercive force magnetic material 103 coexist on one paper sheet 100, it is possible to determine whether a detection signal obtained from a laminated magnetic material has been obtained from the laminated magnetic material 104 including the high-coercive force magnetic material 101 and the middle-coercive force magnetic material 102, or has been obtained from the laminated magnetic material 105 including the high-coercive force magnetic material 101 and the low-coercive force magnetic material 103.

The detection signals obtained from the laminated magnetic materials shown in FIG. 5D and FIG. 5E were explained by taking examples in which the high-coercive force magnetic material 101 existed in the upper layer. However, similar to these examples, the same applies to detection signals obtained from laminated magnetic materials in which the high-coercive force magnetic material 101 exists in the lower layer. In other words, a positional relationship between the laminates does not influence the determination.

As shown in FIG. 5, in order to obtain detection signals having a waveform that can differentiate among the high-coercive force magnetic material 101, the middle-coercive force magnetic material 102, the low-coercive force magnetic material 103, and the laminated magnetic material (104 or 105), for example, as shown in FIG. 1, the direction 201 of the magnetization magnetic field is set at about −160 degrees on an edge of the magnetization magnet 20 and the direction 302 of the bias magnetic field at the position P4 corresponding to the magnetic sensor 10 is set between 30 degrees and 60 degrees.

However, the relationship among the direction 201 of the magnetization magnetic field at the magnetizing position P1, the direction 302 of the bias magnetic field at the position P4 where magnetism is detected, and the transport direction 400 is not limited to the relationship shown in FIG. 1. FIG. 6A to FIG. 6D are views that show the magnetic property determination apparatuses 1 with differently oriented magnetization magnetic fields, differently oriented bias magnetic fields, and different transport directions. FIG. 6A and FIG. 6C show the relationship in examples in which the paper sheet 100 is transported in a forward direction, and FIG. 6B and FIG. 6D show a relationship in examples in which the paper sheet 100 is transported by reverse-direction transport. The term "forward-direction transport" herein denotes to transport in which the angle between the transport direction 400 and the directions 301 and 305 of the bias magnetic field is 90 degrees or less. The term "reverse-direction transport" denotes to transport in which the angle between the transport direction 400 and the directions 303 and 306 of the bias magnetic field is 90 degrees or more.

The forward-direction transport shown in FIG. 6A is an example corresponding to FIG. 1, in which the transport direction 400 is the direction of 0 degrees and the direction 301 of the bias magnetic field at the detection position P4 is between 30 degrees and 60 degrees. In the forward-direction transport, the direction 201 of the magnetization magnetic field is set between −100 degrees and −170 degrees as shown in the left portion of FIG. 6A.

The magnetic detection unit 2 for reverse-direction transport shown in FIG. 6B is in a state in which it is arranged by reversely turning the magnetic detection unit 2 for forward-direction transport shown in FIG. 6A around the Z-axis by 180 degrees. In the example of the reverse-direction transport shown in FIG. 6B, the direction 303 of the bias magnetic field obtained at the detection position P4 is a laterally reversed direction of the magnetic field direction 301 for the forward-direction transport around the Z-axis, i.e., in the direction between 120 degrees and 150 degrees. Similarly, a direction 203 of the magnetization magnetic field at the position P1 at which magnetization is performed is also a laterally reversed direction of the magnetic field direction 201 for the forward-direction transport around the Z-axis, that is, between −10 degrees and −80 degrees. In order to realize the direction 203 of the magnetization magnetic field explained above, the magnetization magnet 20 included in the magnetization unit 3 is arranged above the transport path.

For the magnetic detection unit 2 for the forward-direction transport shown in FIG. 6C, the direction 201 of the magnetization magnetic field is the same as the direction of the magnetization magnetic field for the magnetic detection unit 2 shown in FIG. 6A (between −100 degrees and −170 degrees), but the direction 305 of the bias magnetic field is a vertically reversed direction of the direction 301 of the bias magnetic field of the magnetic detection unit 2 shown in FIG. 6A around the Y-axis, i.e., between −30 degrees and −60 degrees. For the magnetic detection unit 2 for reverse-direction transport shown in FIG. 6D, the direction 203 of the magnetization magnetic field is in the same direction as the magnetic detection unit 2 shown in FIG. 6B (between −10 degrees and −80 degrees), but the direction 306 of the bias magnetic field is a vertically reversed direction of the direction 303 of the bias magnetic field of the magnetic detection unit 2 shown in FIG. 6B around the Y-axis, i.e., between −120 degrees and −150 degrees.

In this manner, by setting the combination of the direction of the bias magnetic field and the direction of the magnetization magnetic field such as from 30 degrees to 60 degrees and from −100 degrees to −170 degrees shown in FIG. 6A, from 120 degrees to 150 degrees and from −10 degrees to −80 degrees shown in FIG. 6B, from −30 degrees to −60 degrees and from −100 degrees to −170 degrees shown in FIG. 6C, or from −120 degrees to −150 degrees and from −10 degrees to −80 degrees shown in FIG. 6D with the transport direction 400 set as 0 degrees, detection signals that can be differentiated among the high-coercive force magnetic material 101, the middle-coercive force magnetic material 102, the low-coercive force magnetic material 103, and the laminated magnetic material (104 or 105) can be obtained as shown in FIG. 5A to FIG. 5E.

In FIG. 6A to FIG. 6D, the high-coercive force magnetic material 101, the middle-coercive force magnetic material 102, and the low-coercive force magnetic material 103 are respectively determined; however, if it is sufficient to differentiate and determine the low-coercive force magnetic material 103 from other magnetic materials, the condition for the range of angles that can be set as the direction of the magnetization magnetic field can be moderated. FIG. 7A to FIG. 7D are views that show relationships between the direction of the magnetization magnetic field and the direction of the bias magnetic field when the magnetic property determination apparatus 1 shown in FIG. 6A to FIG. 6D differentiates and determines the low-coercive force magnetic material 103 from other magnetic materials, i.e., from the high-coercive force magnetic material 101, the middle-coercive force magnetic material 102, and the laminated magnetic material 104. FIG. 7A to FIG. 7D correspond to FIG. 6A to FIG. 6D, respectively.

Figure 7A:
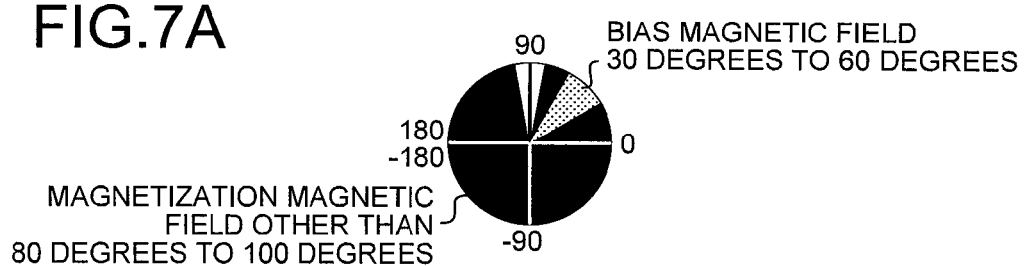
FIGS. 7A, 7B, 7C, and 7D are views that show a direction of the magnetization magnetic field when a magnetic material to be determined by the magnetic property determination apparatus is different from one used in FIG. 6A to FIG. 6D.
Figure 7B:
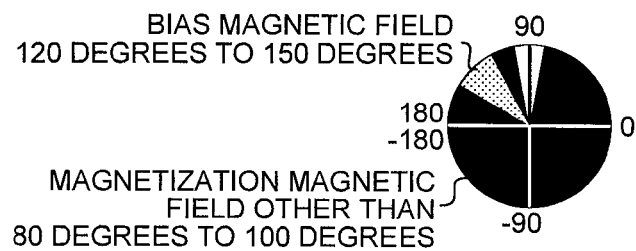
Figure 7C:
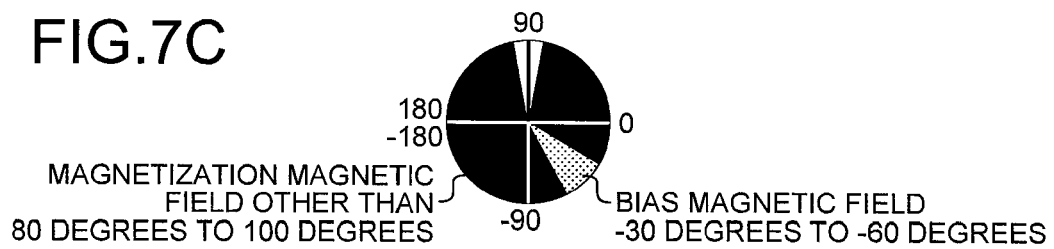
Figure 7D:
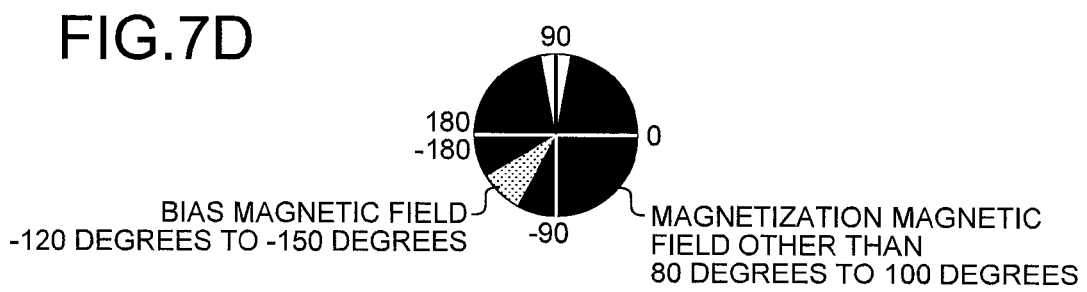

Specifically, when the magnetic property determination apparatus 1 of the forward-direction transport shown in FIG. 6A is required to differentiate and determine the low-coercive force magnetic material 103 from other magnetic materials, the direction of the magnetization magnetic field can be set to a direction other than between 80 degrees and 100 degrees as shown in FIG. 7A. Similarly, when the magnetic property determination apparatuses 1 shown in FIG. 6B to FIG. 6D are to differentiate and determine the low-coercive force magnetic material 103 from other magnetic materials, the direction of the magnetization magnetic field can be set to a direction other than between 80 degrees and 100 degrees as shown in FIG. 7B to FIG. 7D. By performing the setting in this manner, only positive output is obtained for the low-coercive force magnetic material 103 and a part of or all of the outputs of other magnetic materials are negative outputs as shown in FIG. 5, and thereby the magnetic materials can be determined.

Specifically, with the transport direction 400 set at 0 degrees, by setting the direction of the bias magnetic field between 30 degrees and 60 degrees (FIG. 7A) or between 120 degrees and 150 degrees (FIG. 7B) and by setting the direction of the magnetization magnetic field to an angle within a range excluding the angles between 80 degrees and 100 degrees, or by setting the direction of the bias magnetic field between −30 degrees and −60 degrees (FIG. 7C) or between −120 degrees and −150 degrees (FIG. 7D) and by setting the direction of the magnetization magnetic field to an angle within a range excluding the angles between 80 degrees and 100 degrees, the low-coercive force magnetic material 103 can be differentiated from other magnetic materials.

Figure 8A:
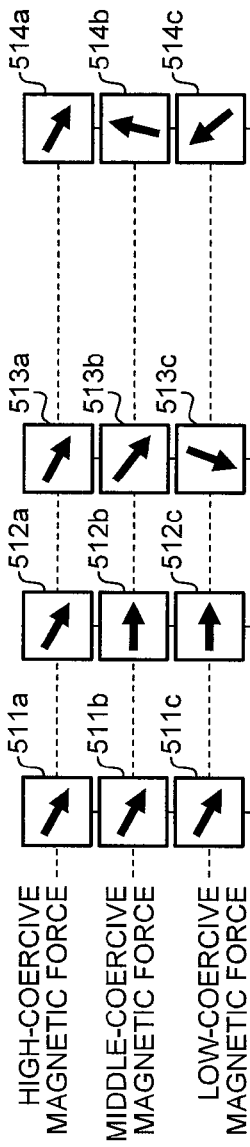
FIGS. 8A and 8B are views that show a magnetic property determination method performed by a magnetic property determination apparatus that transports the paper sheet in the reverse direction.
Figure 8B:
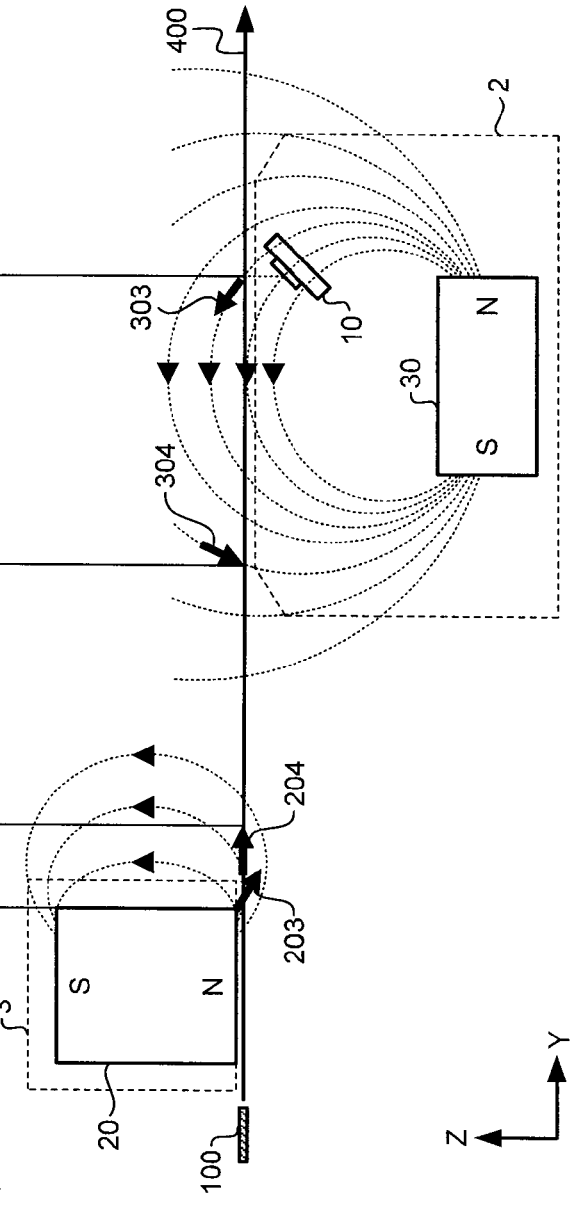

FIG. 8A and FIG. 8B are schematic diagrams that show the magnetic property determination method of the reverse-direction transport shown in FIG. 6B. FIG. 8B shows an outline of the magnetic property determination apparatus 1, and FIG. 8A shows the magnetized states of 3 types of magnetic materials with mutually different coercive forces. For the apparatus configuration, the magnetic property determination apparatus 1 shown in FIG. 8B is different from the magnetic property determination apparatus 1 shown in FIG. 1 in a point such that in the magnetic property determination apparatus 1 shown in FIG. 8B the magnetization unit 3 including the magnetization magnet 20 is arranged above the transport path and in a point such that the magnetic detection unit 2 including the magnetic sensor 10 and the bias magnet 30 is arranged in a reversed manner around the Z-axis. In the magnetic property determination apparatus 1 shown in FIG. 8B, the direction 203 of the magnetization magnetic field and the direction 303 of the bias magnetic field are in a reversed direction of the directions 201 and 302 shown in FIG. 1B around the Z-axis.

If the magnetic material included in the paper sheet 100 is the high-coercive force magnetic material, when the paper sheet 100 is transported under (or on) the magnetization unit 3 in the transport direction 400, the high-coercive force magnetic material is magnetized into the saturation magnetization state or to a state close to the saturation magnetization state when the paper sheet 100 passes the magnetizing position P1 shown in FIG. 8B because the magnetic field intensity of the magnetization magnetic field is very high (4,500 G). In this process, as shown in FIG. 8A, a magnetization direction 511a of the high-coercive force magnetic material is the same direction as the direction 203 of the magnetization magnetic field at the position P1 (about −20 degrees). Even when the paper sheet 100 is transported further in the transport direction 400, no such magnetic field exists that is intense enough to change the magnetized state of the high-coercive force magnetic material thereafter, and thus subsequent magnetization directions 512a, 513a, and 514a remain to be in the same direction as the magnetization direction 511a at the timing of the magnetization, i.e., the direction 203 of the magnetization magnetic field.

If the magnetic material included in the paper sheet 100 is the middle-coercive force magnetic material, the magnetic material is magnetized into the saturation magnetization state at the position P1. However, because the coercive force thereof is small compared with the high-coercive force magnetic material, the paper sheet 100 is continuously influenced by the magnetization magnetic field and the bias magnetic field while the paper sheet 100 is transported in the transport direction 400, and thus a magnetization direction 512b at the position P2 and a magnetization direction 513b at the position P3 vary. Specifically, the magnetization direction 512b at the position P2 is the same as a magnetization direction 204 at the position P2, and the magnetization direction 513b at the position P3 is a direction between the magnetization direction 204 at the position P2 and the direction 304 of the bias magnetic field at the position P3. A final magnetization direction 514b is a direction between the magnetization direction 513b at the position P3 and a subsequent the direction 303 of the bias magnetic field at the position P4. In FIG. 8, although the magnetization intensity is not shown and only the magnetization directions are shown, the coercive force of the middle-coercive force magnetic material is reduced because the direction 303 of the bias magnetic field at the position P4 and the magnetization direction 513b at the position P3 are mutually opposite. As a result, as shown in FIG. 9B, the amplitude of the detection waveform of the middle-coercive force magnetic material is small.

If the magnetic material included in the paper sheet 100 is the low-coercive force magnetic material, because its coercive force is low, the magnetic material is continuously influenced by the magnetization magnetic field and the bias magnetic field while the paper sheet 100 is transported in the transport direction 400, and magnetization directions 511c, 512c, 513c, 514c at respective positions P1 to P4 are in the same directions as the magnetic field directions 203, 204, 304, 303 at the positions P1 to P4, respectively.

As explained above, also in the case of the reverse-direction transport, similarly to the case of forward-direction transport shown in FIG. 1, all of the magnetization direction 514a of the high-coercive force magnetic material, the magnetization direction 514b of the middle-coercive force magnetic material, and the magnetization direction 514c of the low-coercive force magnetic material can be in mutually different directions at the detection position P4 at which the magnetic materials are detected. Accordingly, similarly to the detection signal in the case of the forward-direction transport shown in FIG. 5, detection signals having different waveforms can be obtained among the high-coercive force magnetic material 101, the middle-coercive force magnetic material 102, the low-coercive force magnetic material 103, and the laminated magnetic material (104 or 105).

FIG. 9A to FIG. 9E show waveforms of detection signals obtained in the magnetic property determination apparatus 1 for the reverse-direction transport shown in FIG. 8B when the high-coercive force magnetic material 101, the middle-coercive force magnetic material 102, the low-coercive force magnetic material 103, and the laminated magnetic material 104 or 105 are detected by the magnetic detection unit 2. Outputs of the magnetic sensor 10 are taken on the ordinate axis, time is taken on the abscissa axis, and the waveforms shown in FIG. 9A to FIG. 9E are waveforms of the detection signals outputted from the magnetic sensor 10 when the paper sheet 100 including the respective magnetic materials passes the position P4. Similarly to the example shown in FIG. 5, the respective magnetic materials 101 to 105 corresponding to the detection signals are shown in the upper portion of FIG. 9A to FIG. 9E.

The waveform of the detection signal of the low-coercive force magnetic material 103 shown in FIG. 9C has a positive output for substantially the entire range also in the case of the reverse-direction transport similarly to the case of the forward-direction transport, and the waveform is substantially symmetric in relation to the peak position.

The output of the detection signal of the middle-coercive force magnetic material 102 shown in FIG. 9B is positive for substantially the entire range. The output of the detection signal is positive similarly to the low-coercive force magnetic material 103, and because the waveform thereof is asymmetric in relation to the peak position, the detection signal can be differentiated from the detection signal of the low-coercive force magnetic material 103.

In the detection signal of the high-coercive force magnetic material 101 shown in FIG. 9A, the output changes from a negative output to a positive output. The output of the detection signal is negative for almost the entire detection signal, and thus the detection signal can be differentiated from the detection signal of the low-coercive force magnetic material 103 and the detection signal of the middle-coercive force magnetic material 102.

In the laminated magnetic materials 104 and 105 shown in FIG. 9D and FIG. 9E, the output changes from a negative output to a positive output. The waveform of the laminated magnetic material 104 shown in FIG. 9D is obtained by adding the output of the high-coercive force magnetic material 101 and the waveform of the middle-coercive force magnetic material 102. In contrast, in the laminated magnetic material 105 shown in FIG. 9E, the obtained waveform is a waveform by adding the waveform of the high-coercive force magnetic material 101 and the waveform of the low-coercive force magnetic material 103. In the laminated magnetic materials 104 and 105, both the positive and the negative outputs are obtained similarly to the high-coercive force magnetic material 101 shown in FIG. 9A. However, in the laminated magnetic materials 104 and 105, the amplitude of the positive and the negative outputs are substantially the same which is different from the case of the detection signal of the high-coercive force magnetic material 101. Accordingly, the detection signal of the laminated magnetic materials 104 and 105 can be differentiated from the detection signal of the high-coercive force magnetic material 101.

The magnitude of the detection signal from the middle-coercive force magnetic material 102 changes depending on whether the magnetic sensor 10 is arranged upstream or downstream in the magnetic detection unit 2. That is, when the magnetic sensor 10 is arranged upstream as shown in FIGS. 6A and 6D, the paper sheet 100 reaches the position P4, at which the magnetism is detected, immediately after entering the bias magnetic field. On the contrary, when the magnetic sensor 10 is arranged downstream as shown in FIGS. 6B and 6C, the influence from the bias magnetic field on the middle-coercive force magnetic material 102 becomes high before the paper sheet 100 reaches the position P4 at which the magnetism is detected. Specifically, because the amount of magnetization on the middle-coercive force magnetic material 102 is reduced due to the influence from the bias magnetic field, as can be understood from the comparison between FIG. 5B and FIG. 9B, the amplitude of the detection signal is smaller when the magnetic sensor 10 is arranged downstream than when it is arranged upstream. The high-coercive force magnetic material 101 is not influenced by the bias magnetic field because the magnetic field intensity of the bias magnetic field is smaller than the coercive force of the high-coercive force magnetic material 101.

As explained above, the detection signals having different waveforms are obtained from the magnetic material depending on the position of the magnetic sensor 10 in the magnetic detection unit 2; however, in either cases, a different detection signal is respectively obtained from the high-coercive force magnetic material 101, the middle-coercive force magnetic material 102, the low-coercive force magnetic material 103, and the laminated magnetic materials (104 and 105). As a result, the respective magnetic materials 101 to 103, and the laminated magnetic materials 104 and 105 can be determined based on the detection signal.

The determination among the respective magnetic materials of the high-coercive force magnetic material 101, the middle-coercive force magnetic material 102, and the low-coercive force magnetic material 103 and the laminated magnetic material (104 or 105) based on the detection signal is performed by using the amplitude of the detection signal and the symmetry of the signal waveform in relation to the peak position. For example, if the amplitude at the peak position on the negative side is larger than a specific value, and if almost the entire detection signal is the negative output, then it is determined that the magnetic material is the high-coercive force magnetic material 101 based on the ratio between the time in which the negative output is obtained and the time in which the positive output is obtained. Otherwise, it is determined that the magnetic material is the laminated magnetic material 104. On the contrary, if the amplitude at the peak position on the negative side is smaller than a specific value, if the waveform on the positive side is substantially symmetric in relation to the peak position, then it is determined that the magnetic material is the low-coercive force magnetic material 103, and if the waveform on the positive side is substantially asymmetric in relation to the peak position, then it is determined that the magnetic material is the middle-coercive force magnetic material 102. The method for determining the symmetry of the signal waveform is not particularly limited, and the symmetry can be determined by comparing the distance from the peak position to a position at which the amplitude becomes 0 (zero) for the both directions, or the symmetry can be determined based on the correlation with the waveform obtained by reversing the original waveform in the lateral direction around the peak position as the axis.

According to the magnetic property determination apparatus 1 of the present embodiment, the high-coercive force magnetic material, the middle-coercive force magnetic material, the low-coercive force magnetic material, and the laminated magnetic material can be differentiated and determined from one another. Therefore, the type of the magnetic material included in the paper sheet 100 can be determined even if the magnetic material included in the paper sheet 100 is different according to the type of the paper sheet 100, and thus the authenticity of the paper sheet 100 can be determined. Moreover, if any pattern has been drawn on the paper sheet 100 by using the respective magnetic materials, the pattern can be recognized. Furthermore, if any code has been formed by a combination of the magnetic materials, the code can be recognized by correctly determining the respective magnetic materials.

As explained above, according to the present embodiment, the magnetic field intensity and the direction of the magnetization magnetic field generated by the magnetization unit 3 are appropriately set and the magnetic field intensity and the direction of the bias magnetic field by the magnetic detection unit 2 are appropriately set, and thereby the magnetization directions of the respective magnetic materials can be controlled to be different at the position at which the magnetism is detected by the magnetic detection unit 2. Accordingly, the respective magnetic materials can be differentiated and determined from one another based on the characteristic of the detection signal obtained when the magnetism is detected.

For example, the magnetic field intensity of the magnetization magnetic field is set to an intensity for magnetizing the high-coercive force magnetic material into the saturation magnetization state, the magnetic field intensity of the bias magnetic field is set to an intensity for magnetizing the low-coercive force magnetic material into the saturation magnetization state and for not magnetizing the middle-coercive force magnetic material into the saturation magnetization state. Moreover, the direction of the bias magnetic field at the position at which the magnetic material is detected by the magnetic detection unit 2 is set in mutually different direction from the magnetic field direction at which the respective magnetic material is magnetized. Accordingly, the high-coercive force magnetic material, the middle-coercive force magnetic material, the low-coercive force magnetic material, and the laminated magnetic material can be differentiated and determined from one another based on the amplitude and the waveform of the detection signal.

For example, the respective magnetic materials can be determined based on the detection signal obtained by one magnetic sensor 10 by realizing the above-explained magnetization magnetic field by using only one magnetization magnet 20. Therefore, thus reduction in the size and the cost of the magnetic property determination apparatus 1 can be achieved.

Second Embodiment

Figure 10A:
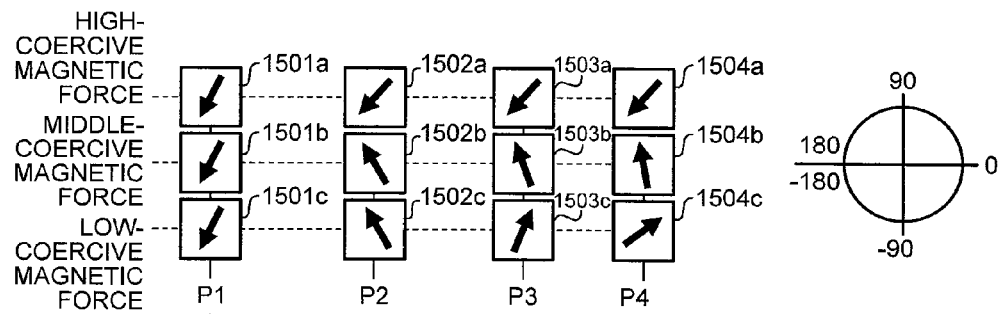
FIGS. 10A, 10B, and 10C are views that show a magnetic property determination method performed by a magnetic property determination apparatus according to a second embodiment.
Figure 10B:
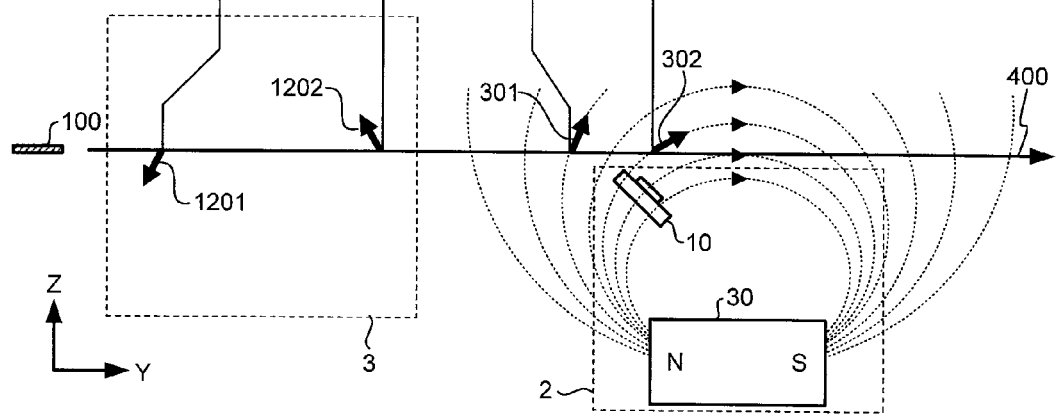
Figure 10C:
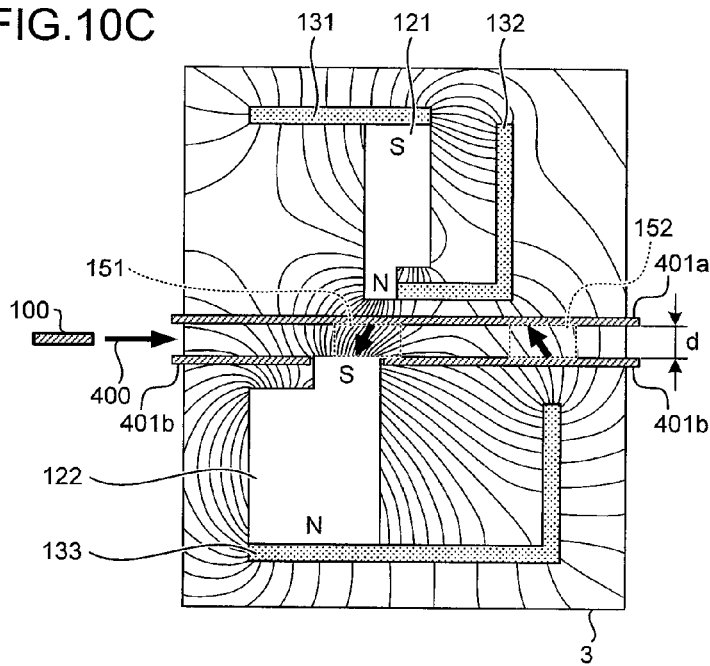

Next, another example of the magnetic property determination apparatus 1 that can detect magnetic materials with mutually different coercive forces based on the same principle as the first embodiment will be explained. FIG. 10A to FIG. 10C are schematic diagrams that show a magnetic property determination method performed by the magnetic property determination apparatus 1 according to the present embodiment. FIG. 10B shows an outline of the magnetic property determination apparatus 1, FIG. 10A shows the magnetized state of the 3 types of magnetic materials with mutually different coercive forces, and FIG. 10C shows a configuration of the magnetization unit 3 and a magnetic field distribution of the magnetization magnetic field generated by the magnetization unit 3. Moreover, FIG. 11 is a perspective view indicating a schematic configuration of the magnetization unit 3.

Figure 11:
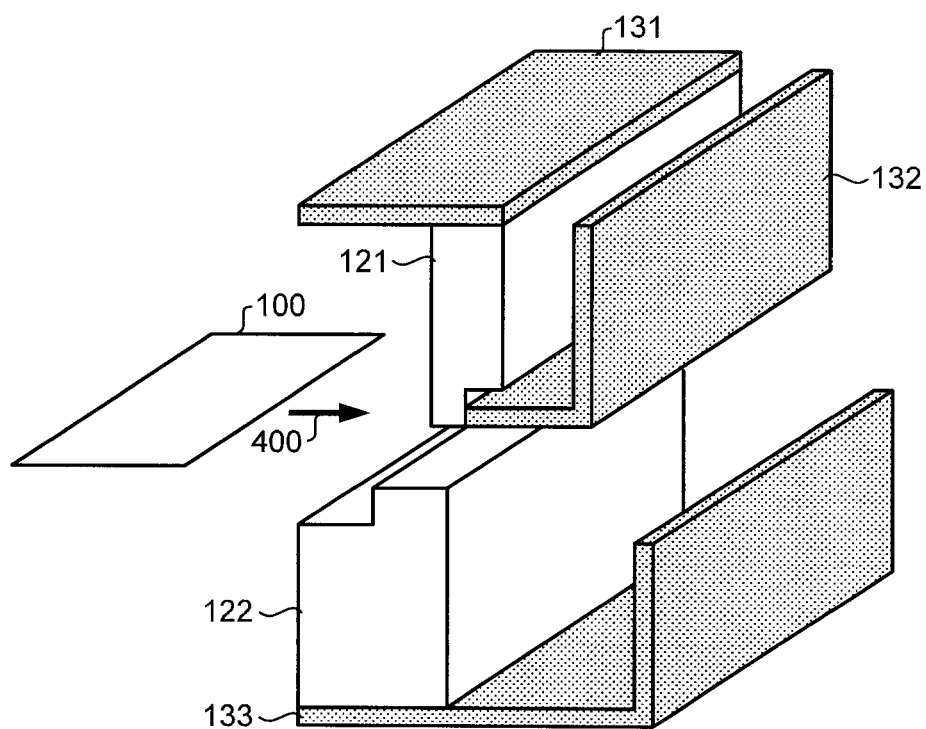
FIG. 11 is a perspective view indicating a schematic configuration of a magnetization unit according to a second embodiment.

As shown in FIG. 10C and FIG. 11, in the magnetization unit 3, across the transport path on which the paper sheet 100 is transported in the transport direction 400, a first magnet (magnetization magnet) 121 and two magnetically permeable members (yokes) 131, 132 are arranged on an upper side, and a second magnet (magnetization magnet) 122 and one magnetically permeable member (yoke) 133 are arranged on a lower side. For example, a material having a high magnetic permeability, such as an iron plate, can be used as the magnetically permeable members 131 to 133.

When seen from a side (X axis direction) that is orthogonal to the transport direction 400 of the paper sheet 100, the first magnet 121 has a side surface shape in which a cutout portion is formed in a downstream end in the transport direction of a bottom surface opposing the transport path (a lower right corner of the first magnet 121 in the drawing). As a result, on the bottom surface of the first magnet 121 are formed a magnetic-pole surface that is located upstream in the transport direction and parallel to a transport surface (XY plane), and another magnetic-pole surface that is located downstream in the transport direction and parallel to the transport surface. The magnetically permeable member 132 having an inverted L-shape, that is, having a side surface shape that looks like an inverted letter L, is arranged with a slight gap between the cutout portion in the first magnet 121. The bottom surface of the first magnet 121 and the bottom surface of the magnetically permeable member 132 of inverted L-shape constitute one surface that is parallel to the transport surface. Moreover, on a top surface of the first magnet 121 is provided the magnetically permeable member 131 having a rectangular side surface shape that elongates in the transport direction. A bottom surface on the downstream side in the transport direction of the magnetically permeable member 131 contacts a top surface of the first magnet 121.

When seen from a side (X axis direction), the second magnet 122 has a shape in which a cutout portion is formed in an upstream end in the transport direction of a top surface opposing the transport path (an upper left corner of the second magnet 122 in the drawing). As a result, in the second magnet 122 are formed a magnetic-pole surface that is located downstream in the transport direction and parallel to the transport surface (XY plane), and another magnetic-pole surface that is located upstream in the transport direction and parallel to the transport surface. The magnetically permeable member 133 having an inverted L-shape and constituted by a vertical part and a lower horizontal part is arranged in a bottom surface side of the second magnet 122 such that a top surface of the lower horizontal part touches the bottom surface of the second magnet 122. A vertical surface of the lower horizontal part of the magnetically permeable member 133 of inverted L-shape in the upstream side of the transport direction and a vertical surface of the second magnet 122 in the upstream side of the transport direction constitute one surface. A top surface of the vertical part of the magnetically permeable member 133 of inverted L-shape is located at a position that is lower, for example, by about 1 mm, than the magnetic-pole surface on the downstream side in the transport direction of the second magnet 122.

The first magnet 121 and the second magnet 122 are arranged so as to be shifted in the transport direction. Specifically, the top magnetic-pole surface of the second magnet 122 that is closest to the transport path and the bottom magnetic-pole surface of the first magnet 121 that is closest to the transport path are arranged so that only a part of these magnetic-pole surfaces face each other across the transport path whereby the second magnet 122 is shifted on the upstream side in the transport direction than the first magnet 121. A first magnetic field region 151 shown in FIG. 10C is formed between the top magnetic-pole surface of the second magnet 122 that is closest to the transport path and the bottom magnetic-pole surface of the first magnet 121 that is closest to the transport path.

The magnetically permeable member 132 of the inverted L-shape arrange above the transport path is constituted by a vertical part and a lower horizontal part. The vertical part of the magnetically permeable member 132 is arranged on the upstream side of the transport direction from the vertical part of the magnetically permeable member 133 of the inverted L-shape arranged below the transport path. A second magnetic field region 152 shown in FIG. 10C is formed between a bottom surface of the vertical part of the magnetically permeable member 132 arranged above the transport path and the top surface of the vertical part of the magnetically permeable member 133 arranged below the transport path.

The first magnetic field region 151 and the second magnetic field region 152 are parts of the magnetization magnetic field formed by the magnetization unit 3. A magnetic field direction 1201 shown in FIG. 10A corresponds to the first magnetic field region 151 shown in FIG. 10C, and a magnetic field direction 1202 shown in FIG. 10A corresponds to the second magnetic field region 152 shown in FIG. 10C.

A magnetic field distribution of the magnetization magnetic field by the first magnet 121 and the two magnetically permeable members 131 and 132, and the second magnet 122 and the magnetically permeable member 133 is as indicated with contour lines in FIG. 10C. The paper sheet 100 is transported in the transport path, which has a width d of about 2 mm from the top surface of the second magnet 122, toward the transport direction 400 between the first magnet 121 and the second magnet 122. As shown in FIG. 10C, the transportation of the paper sheet 100 is regulated by a top transport guide 401a and a bottom transport guide 401b. The transport guides 401a and 401b are made of, for example, resin. Because the paper sheet 100 passes through a space regulated by the transporting guide 401a and 401b, jamming of the transport path (paper sheet jamming) can be reduced.

In this manner, the present embodiment is different from the first embodiment in that the magnetization unit 3 includes a plurality of the magnets 121 and 122 and a plurality of the magnetically permeable members 131 to 133 that are arranged above and below and sandwiching the transport path. In the present embodiment, the first magnetic field region 151 corresponding to the magnetic field direction 201 of the first embodiment is formed by the plurality of the magnets 121 and 122, and the second magnetic field region 152 corresponding to the magnetic field direction 202 of the first embodiment is formed by the plurality of the magnetically permeable members 132 and 133. In the following, the features according to the present embodiment are explained and an explanation overlapping with the first embodiment is omitted.

The magnetization unit 3 is configured so that an intensity of the magnetization magnetic field at a position P1 shown in FIG. 10B, namely an intensity in the first magnetic field region 151 shown in FIG. 10C, is the maximum. Specifically, the magnetization unit 3 is set so that a magnetic field intensity (4,500 G or more) at the position P1 in the transport path is 1.5 times or more of the coercive force (3,000 Oe) of the high-coercive force magnetic material. Moreover, the magnetization unit 3 is set so that a magnetic field intensity (450 G to 3,000 G) at a position P2 shown in FIG. 10B, namely an intensity in the second magnetic field region 152 shown in FIG. 10C, is 1.5 times or more of the coercive force (300 Oe) of the middle-coercive force magnetic material and 1 time or lower of the coercive force of the high-coercive force magnetic material.

The magnetization unit 3 generates the magnetization magnetic field so that the magnetic field direction 1201 of the magnetization magnetic field at the position P1 is between −100 degrees and −170 degrees and the magnetic field direction 1202 of the magnetization magnetic field at the position P2 is between 100 degrees and 180 degrees. For example, it is preferable that the magnetic field direction 1201 at the position P1 is near −120 degrees and the magnetic field direction 1202 at the position P2 is near 120 degrees. In the following explanation, the magnetic field direction 1201 at the position P1 is −120 degrees and the magnetic field direction 1202 at the position P2 is 120 degrees.

One feature of the present embodiment is that the magnetization magnetic field generated by the magnetization unit 3 includes the first magnetic field region 151 at the position P1 in the transport path and the second magnetic field region 152 at the position P2 in the transport path that is downstream than the position P1 in the transport direction, and that the magnetic field intensities and the magnetic field directions of the first magnetic field region 151 are different from those of the second magnetic field region 152.

As a result, as shown in FIG. 10A, if the magnetic material included in the paper sheet 100 is the high-coercive force magnetic material, a magnetization direction 1501a of the high-coercive force magnetic material at the position P1 is in the same direction (about −120 degrees) as the magnetic field direction 1201 at the position P1 of the first magnetic field region 151. The paper sheet 100 is further transported in the transport direction 400, and because the magnetic field intensity of the magnetization magnetic field gradually weakens, the magnetized state of the high-coercive force magnetic material does not vary, and magnetization directions 1502a, 1503a, and 1504a at the positions P2 to P4, respectively, are in the same direction as the magnetization direction 1501a at the position P1.

If the magnetic material included in the paper sheet 100 is the middle-coercive force magnetic material, because the magnetic material is magnetized into the saturation magnetization state at the position P1 similarly to the case of the high-coercive force magnetic material, a magnetization direction 1501b is in the same direction (about −120 degrees) as the magnetic field direction 1201 of the first magnetic field region 151. However, because the coercive force of the middle-coercive force magnetic material is lower than that of the high-coercive force magnetic material, the middle-coercive force magnetic material is continuously influenced by the magnetization magnetic field while being transported in the transport direction 400. Accordingly, when the paper sheet 100 passes the position P2, a magnetization direction 1502b of the middle-coercive force magnetic material is in the same direction (about 120 degrees) as the magnetic field direction 1202 of the second magnetic field region 152. As the paper sheet 100 is further transported, the paper sheet 100 is influenced by the bias magnetic field, and at the position P3, the magnetization direction of the paper sheet 100 becomes a magnetization direction 1503b, which is a direction reached by slightly turning from the second magnetization direction 1502b at the position P2 toward the direction 301 of the bias magnetic field at the position P3. Also at the position P4, the magnetization direction turns to a magnetization direction 1504b reached by slightly turning from the magnetization direction 1503b at the position P3 toward the direction 302 of the bias magnetic field at the position P4. However, because the magnetic field intensity of the bias magnetic field (450 G) is lower than the magnetic field intensity (300 Oe) necessary for magnetizing the coercive force of the middle-coercive force magnetic material into the saturation magnetization state, a final magnetic field direction of the middle-coercive force magnetic material becomes the magnetization direction 1504b that is a direction between the magnetization direction 1502b (about 120 degrees) at the position P2 in the second magnetic field region 152 and the direction 302 (between 30 degrees and 60 degrees) of the bias magnetic field at the position P4.

If the magnetic material included in the paper sheet 100 is the low-coercive force magnetic material, the magnetic material is magnetized into the saturation magnetization state at the position P1 similarly to the cases of other magnetic materials, and a magnetization direction 1501c (about −120 degrees) is in the same direction as the magnetic field direction 1201 in the first magnetic field region 151. However, because the coercive force of the low-coercive force magnetic material is low, the magnetic material is continuously influenced by the magnetization magnetic field while the paper sheet 100 is transported in the transport direction 400. Accordingly, similarly to the middle-coercive force magnetic material, a magnetization direction 1502c at the timing of passage over the position P2 is in the same direction (about 120 degrees) as the magnetic field direction 1202 in the second magnetic field region 152. As the paper sheet 100 is further transported, the paper sheet 100 is influenced by the bias magnetic field, and at the position P3, the magnetization direction becomes the same magnetization direction 1503c as the direction 301 of the bias magnetic field. Also at the position P4, the magnetization direction becomes the same magnetization direction 1504c as the direction 302 of the bias magnetic field. The magnetic field intensity of the bias magnetic field (450 G) is sufficiently higher than the coercive force (50 Oe) of the low-coercive force magnetic material, so that the low-coercive force magnetic material is magnetized into the saturation magnetization state at the respective positions. Accordingly, the magnetization directions of the low-coercive force magnetic material at the respective positions are in the same direction as the direction of the bias magnetic field at the respective positions.

As explained above, also in the present embodiment, similarly to the first embodiment, at the detection position P4 at which the detection is performed by the magnetic detection unit 2, the magnetization directions of the magnetic materials can be set according to the coercive force thereof. As explained above in the first embodiment, the type of the magnetic material can be determined based on the detection signal for the magnetic material that passes through the transport path.

Next, the reason why it is preferable if the direction 1201 of the magnetization magnetic field at the position P1 is about −120 degrees and the magnetic field direction 1202 is about 120 degrees will be explained. As shown in FIG. 10A, at the position P4 at which the magnetic material included in the paper sheet 100 is detected by the magnetic detection unit 2, the magnetization direction 1504a of the high-coercive force magnetic material is in the same direction as the magnetic field direction 1201 at the position P1 in the first magnetic field region 151, and the magnetization direction 1504b of the middle-coercive force magnetic material is a direction reached by slightly turning from the magnetic field direction 1202 at the position P2 in the second magnetic field region 152 toward the direction 302 of the bias magnetic field.

Figures 12A, 12B, 12C, 12D:
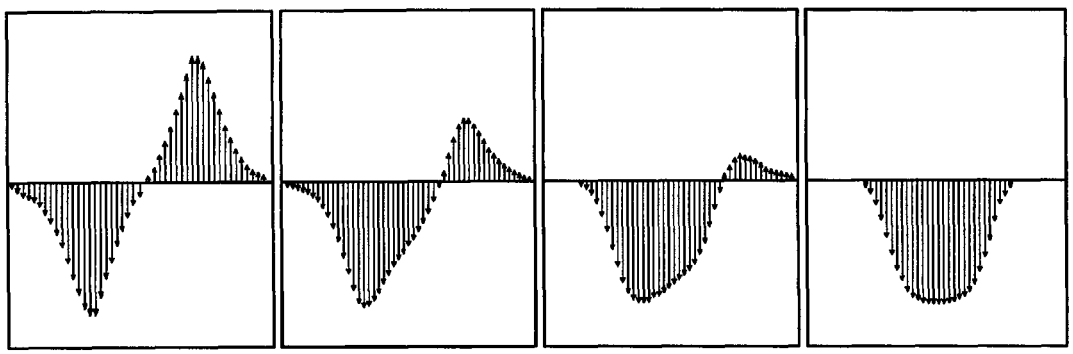
FIGS. 12A, 12B, 12C, 12D, 12E, 12F, 12G, and 12H are views that show magnetized states of a high-coercive force magnetic material and a middle-coercive force magnetic material when a magnetization direction of the magnetic material has a specific angle.
Figures 12E, 12F, 12G, 12H:
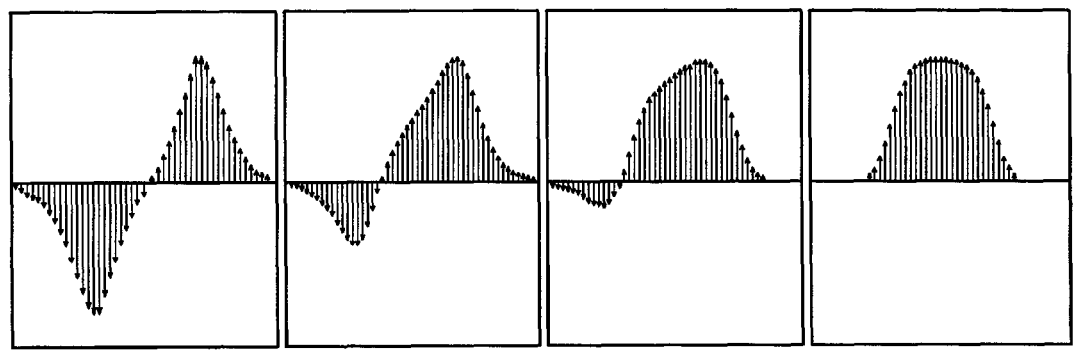

Among FIG. 12A to FIG. 12H, FIG. 12A to FIG. 12D show the distribution of the magnetic field in the Z-axis direction around immediately below the high-coercive force magnetic material (around immediately below the magnetic material by a clearance of 0.5 mm) having been magnetized in magnetization directions 1507 to 1510, respectively, and FIG. 12E to FIG. 12H show the distribution of the magnetic field in the Z-axis direction around immediately below the middle-coercive force magnetic material (around immediately below the magnetic material by a clearance of 0.5 mm) having been magnetized in magnetization directions 1511 to 1514, respectively. Specifically, the magnetization direction 1507 shown in FIG. 12A is −180 degrees, the magnetization direction 1508 of FIG. 12B is −160 degrees, the magnetization direction 1509 of FIG. 12C is −120 degrees, and the magnetization direction 1510 of FIG. 12D is −90 degrees. The magnetization direction 1511 shown in FIG. 12E is 180 degrees, the magnetization direction 1512 of FIG. 12F is 160 degrees, the magnetization direction 1513 of FIG. 12G is 120 degrees, and the magnetization direction 1514 of FIG. 12H is 90 degrees. If the magnetic field direction 1201 at the position P1 shown in FIG. 10B is set at −180 degrees, −160 degrees, −120 degrees, and −90 degrees, the magnetic field distribution of the high-coercive force magnetic material at the position P4 will be as shown in FIG. 12A to FIG. 12D, and if the magnetic field direction 1202 at the position P2 is set at 180 degrees, 160 degrees, 120 degrees, and 90 degrees, the magnetic field distribution of the middle-coercive force magnetic material at the position P4 will be substantially the same as the distribution shown in FIG. 12E to FIG. 12H. The magnetic field distribution is detected by the magnetic detection unit 2.

The magnetic signal is detected in the magnetic detection unit 2 so that the shapes of the magnetic field distributions shown in FIG. 12A to FIG. 12D are followed from left to right. As shown in FIG. 12B, the high-coercive force magnetic material having been magnetized into the magnetization direction 1508 oriented toward −160 degrees, an overshoot magnetic signal corresponding to the magnetic field distribution on the positive side is detected after a magnetic signal corresponding to the magnetic field distribution on the negative side is detected. The overshoot magnetic signal in the magnetic field distribution shown in FIG. 12C corresponding to the magnetic material having been magnetized in the magnetization direction 1509 of −120 degrees is smaller than the overshoot magnetic signal in the magnetic field distribution shown in FIG. 12B corresponding to the magnetic material having been magnetized in the magnetization direction 1508 of −160 degrees, and thus it is more preferable that the magnetization direction is −120 degrees rather than −160 degrees.

Similarly, in the magnetic detection unit 2, the magnetic signal is detected so as to follow the shape of the magnetic field distribution shown in FIG. 12E to FIG. 12H from right to left. As shown in FIG. 12F, in the middle-coercive force magnetic material having been magnetized in the magnetization direction 1512 of 160 degrees, an overshoot magnetic signal corresponding to the magnetic field distribution on the negative side is detected after a magnetic signal corresponding to the magnetic field distribution on the positive side is detected. The overshoot magnetic signal in the magnetic field distribution shown in FIG. 12G corresponding to the magnetic material having been magnetized in the magnetization direction 1513 of 120 degrees is smaller than the overshoot magnetic signal in the magnetic field distribution shown in FIG. 12F corresponding to the magnetic material having been magnetized in the magnetization direction 1512 of 160 degrees, and thus it is more preferable that the magnetization direction is about 120 degrees rather than 160 degrees.

If the overshoot only is considered, FIG. 12D in which the magnetization direction 1510 is −90 degrees is more preferable than FIG. 12C in which the magnetization direction 1509 is −120 degrees if the magnetic material is the high-coercive force magnetic material. Similarly, FIG. 12H in which the magnetization direction 1514 is 90 degrees is more preferable than FIG. 12G in which the magnetization direction 1513 is 120 degrees if the magnetic material is the middle-coercive force magnetic material. However, if the magnetic field direction 1201 of the first magnetic field region 151 is set at −90 degrees and the magnetic field direction 1202 of the second magnetic field region 152 is set at 90 degrees, the detected waveform becomes a waveform obtained by adding the waveforms of the magnetic field distributions shown in FIG. 12D and FIG. 12H if a laminated magnetic material obtained by laminating the high-coercive force magnetic material and the middle-coercive force magnetic material is to be detected, and thus the magnetic field distributions are set off, and therefore the laminated magnetic material cannot be detected. Accordingly, in the present embodiment, in order to determine the high-coercive force magnetic material, the middle-coercive force magnetic material, and the laminated magnetic material including the high-coercive force magnetic material and the middle-coercive force magnetic material, respectively, based on the detection signal at the position P4, the magnetic field direction 1201 at the position P1 is set at about −120 degrees and the magnetic field direction 1202 at the position P2 is set at about 120 degrees.

As explained above in the first embodiment with reference to FIG. 1 and FIG. 8, the relationship among the directions 1201 and 1202 of the magnetization magnetic field, the direction 302 of the bias magnetic field at the position P4 at which the magnetism is detected, and the transport direction 400 are not limited to those in the case of the forward-direction transport shown in FIG. 10. That is, those for the reverse-direction transport can be used.

Figure 13A:
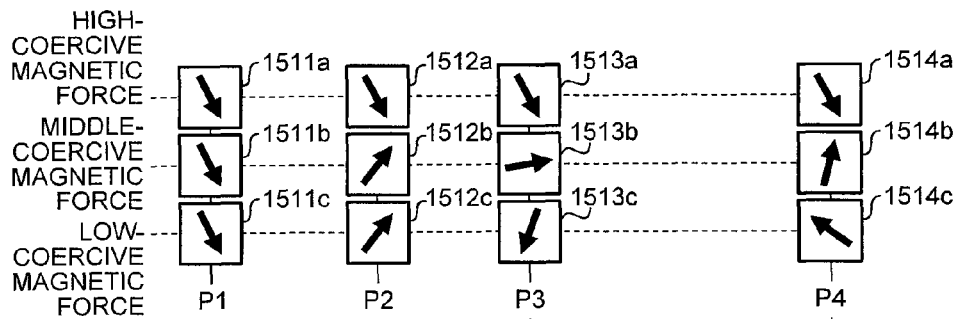
FIGS. 13A, 13B, and 13C are views that show a magnetic property determination method with reverse-direction transport according to the second embodiment.
Figure 13B:
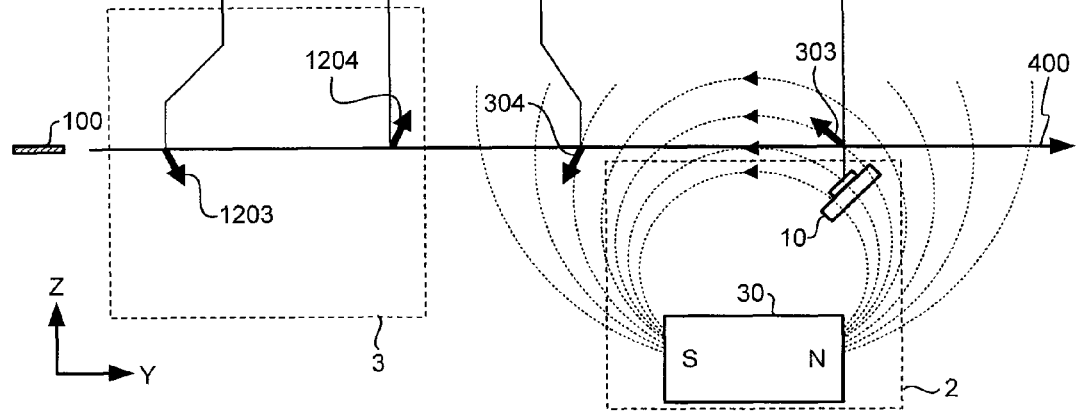
Figure 13C:
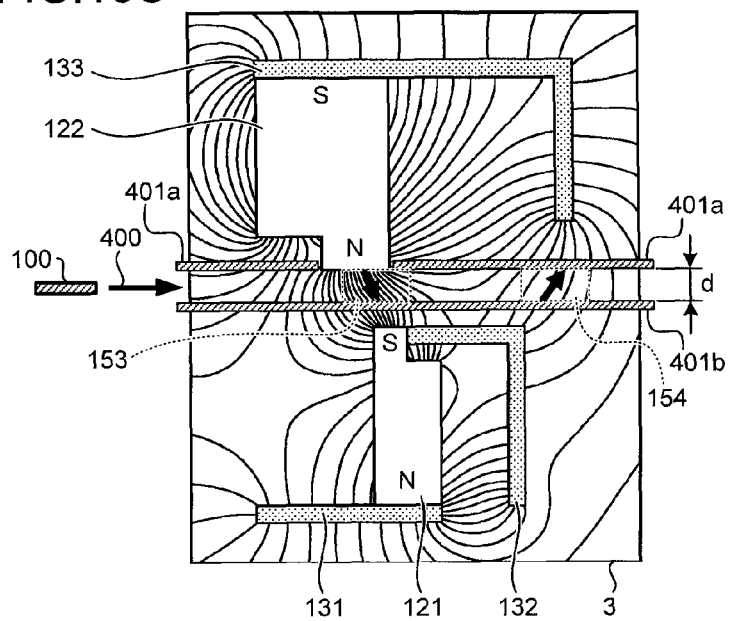
Figure 14A:
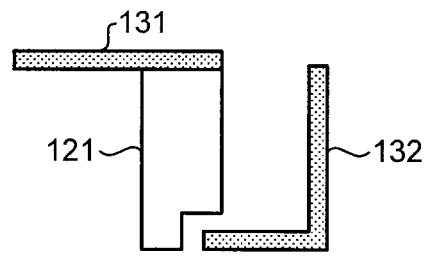
FIGS. 14A, 14B, 14C, and 14D are views that show examples of arrangement of a magnetization magnet and a magnetically permeable member on an upper side of a transport path.
Figure 14B:
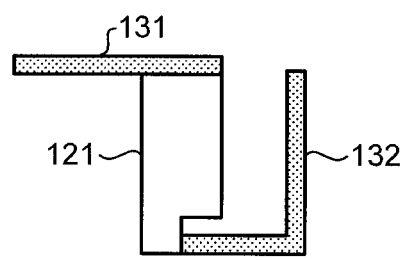
Figure 14C:
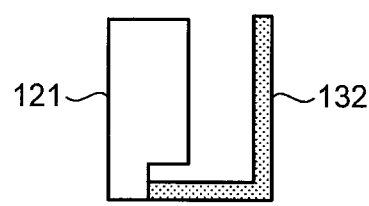
Figure 14D:
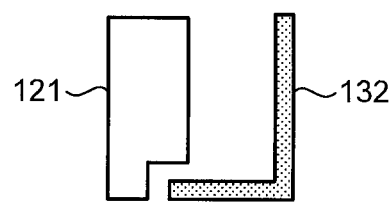

FIG. 13A to FIG. 13C are schematic diagrams that show the magnetic property determination method in the case of the reverse-direction transport. FIG. 13B shows an outline of the magnetic property determination apparatus 1, FIG. 13A shows the magnetized state of the 3 types of magnetic materials with mutually different coercive forces, and FIG. 13C shows a configuration of the magnetization unit 3 and a magnetic field distribution of the magnetization magnetic field generated by the magnetization unit 3. The configuration of the magnetic property determination apparatus 1 shown in FIG. 13B is different from the magnetic property determination apparatus 1 shown in FIG. 10B in that in the magnetic property determination apparatus 1 shown in FIG. 13B the magnetization unit 3 is arranged vertically reversed around the Y-axis with respect to the transport path and that the magnetic detection unit 2 is arranged laterally reversed around the Z-axis. In the magnetic property determination apparatus 1 shown in FIG. 13B, directions 1203 and 1204 of the magnetization magnetic field and the direction 303 of the bias magnetic field are vertically reversed around the Z-axis from the directions 1201 and 1202 of the magnetization magnetic field and the direction 302 of the bias magnetic field shown in FIG. 10B.

If the magnetic material included in the paper sheet 100 is the high-coercive force magnetic material, when the paper sheet 100 is transported in the transport direction 400, because the magnetic field intensity of the magnetization magnetic field (4,500 G) is very high, the magnetic material is magnetized into the saturation magnetization state or into a magnetized state close to the saturation magnetization state when the paper sheet 100 passes the position P1 shown in FIG. 13B. In this process, a magnetization direction 1511$a$ of the high-coercive force magnetic material is in the same direction (about −60 degrees) as the direction 1203 of the magnetization magnetic field at the position P1. When the paper sheet 100 is transported further in the transport direction 400, no such magnetic field exists that is intense enough to change the magnetized state of the high-coercive force magnetic material thereafter, and thus subsequent magnetization directions 1512$a$, 1513$a$, and 1514$a$ remain to be in the same direction as the magnetization direction 1511$a$ at the timing of the magnetization, i.e., the direction 1203 of the magnetization magnetic field.

If the magnetic material included in the paper sheet 100 is the middle-coercive force magnetic material, the magnetic material is magnetized into the saturation magnetization state at the position P1. However, because the coercive force of the middle-coercive force magnetic material is low compared with the high-coercive force magnetic material, the magnetic material is continuously influenced by the magnetization magnetic field and the bias magnetic field while the paper sheet 100 is transported in the transport direction 400, and thus a magnetization direction 1512$b$ at the position P2 and a magnetization direction 1513$b$ at the position P3 vary. Specifically, the magnetization direction 1512$b$ at the position P2 is the magnetic field direction 1204 at the position P2 (about 60 degrees), and the magnetization direction 1513$b$ at the position P3 is a direction between the magnetic field direction 1204 at the position P2 and the direction 304 of the bias magnetic field at the position P3. A final magnetization direction 1514$b$ is a direction between the magnetization direction 1513$b$ at the position P3 and the direction 303 of the bias magnetic field at the subsequent position P4. Because the magnetic field direction 303 at the position P4 and the magnetization direction 1513$b$ at the position P3 are opposite, the coercive force of the middle-coercive force magnetic material is weakened, and thus the amplitude of the detection waveform of the middle-coercive force magnetic material is lower than that in the forward-direction transport.

If the magnetic material included in the paper sheet 100 is the low-coercive force magnetic material, because the coercive force of the low-coercive force magnetic material is low, the magnetic material is continuously influenced by the magnetization magnetic field and the bias magnetic field while the paper sheet 100 is transported in the transport direction 400, and thus magnetization directions 1511$c$ to 1514$c$ at the respective positions P1 to P4 are the same as the magnetic field directions 1203, 1204, 304, and 303 at the position.

Accordingly, also in the case of the reverse-direction transport, similarly to the case of the forward-direction transport shown in FIG. 10, all of the magnetization direction 1514$a$ of the high-coercive force magnetic material, the magnetization direction 1514$b$ of the middle-coercive force magnetic material, and the magnetization direction 1514$c$ of the low-coercive force magnetic material can be set in the mutually different directions. Accordingly, detection signals having different waveforms can be obtained among the high-coercive force magnetic material, the middle-coercive force magnetic material, the low-coercive force magnetic material, and the laminated magnetic materials.

The configuration of the magnets 121 and 122 and the magnetically permeable members 131 to 133 constituting the magnetization unit 3 is not limited to the one shown in FIG. 10A to FIG. 11 as long as the above-explained magnetic field intensities and the magnetic field directions can be realized with the first magnetic field region 151 and the second magnetic field region 152. FIG. 14A to FIG. 14D are views showing examples of a configuration including the first magnet 121 shown in FIG. 10A to FIG. 11 above the transport path. Moreover, FIG. 15A to FIG. 15D are views showing examples of a configuration including the second magnet 122 shown in FIG. 10A to FIG. 11 below the transport path. FIG. 10A to FIG. 11 show the magnetization unit 3 that is realized by a combination of the configuration shown in FIG. 14B and the configuration shown in FIG. 15A; however, the magnetization unit 3 can be realized by a desired combination of a configuration selected from FIG. 14A to FIG. 14D and a configuration selected from FIG. 15A to FIG. 15D.

Figure 15A:
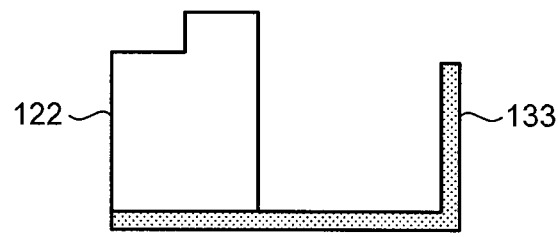
FIGS. 15A, 15B, 15C, and 15D are views that show examples of arrangement of a magnetization magnet and a magnetically permeable member arranged on a lower side of the transport path.
Figure 15B:
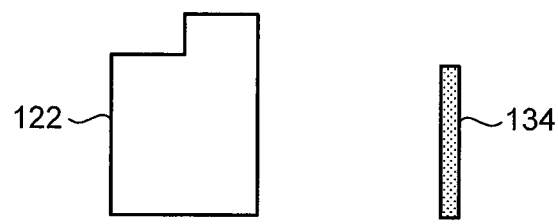
Figure 15C:
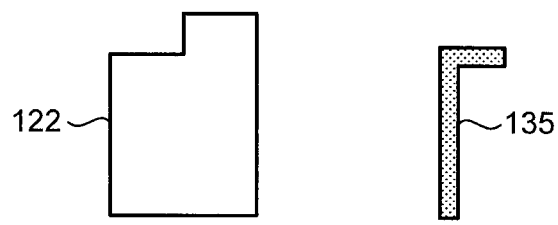
Figure 15D:
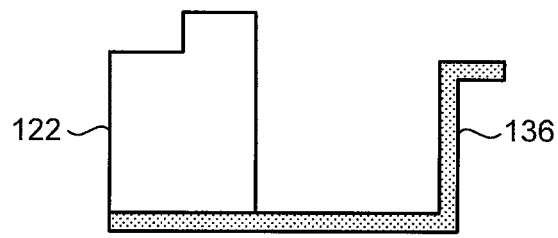

FIG. 14A to FIG. 15D show a side surface shape of each configuration in a situation in which the transport direction 400 of the paper sheet 100 is in the right direction in the horizontal plane of the drawings. The configuration in FIG. 14B is different from the configuration in FIG. 14A in that the magnetically permeable member 132 contacts the first magnet 121. The configuration in FIG. 14C is obtained by removing the magnetically permeable member 131 arranged above the first magnet 121 of the configuration in FIG. 14B. The configuration in FIG. 14D is obtained by removing the magnetically permeable member 131 of the configuration in FIG. 14A. Moreover, the configuration in FIG. 15B is different from the configuration in FIG. 15A in that a magnetically permeable member 134 has an I-shape, that is, without the bottom part of the magnetically permeable member 133 shown in FIG. 15A. FIG. 15C shows a configuration in which an L-shape magnetically permeable member 135 is arranged in a reverse manner. FIG. 15D shows a configuration in which an S-shaped magnetically permeable member 136 is arranged so as to contact the bottom surface of the second magnet 122.

As explained above, according to the present embodiment, the magnetic field intensities and the shapes of the magnets 121 and 122, the shapes of the magnetically permeable members 131 to 136, the arrangement relations among the magnets 121 and 122 and the magnetically permeable members 131 to 136, and the like, are set appropriately, so that the magnetic field direction 1201 has a predetermined angle and the magnetic field intensity of the first magnetic field region 151 is appropriate magnetic field intensity in the first magnetic field region 151 at the position P1 on the upstream side in the transport direction 400, and the magnetic field direction 1202 has a predetermined angle and the magnetic field intensity of the second magnetic field region 152 is appropriate magnetic field intensities at the position P2 in the downstream than the position P1. Therefore, the magnetization directions of the respective magnetic materials can be set to mutually different directions at the position P4 at which magnetism is detected by the magnetic detection unit 2 according to the coercive force. Accordingly, the type of the magnetic materials with mutually different coercive forces can be determined based on the characteristics of the detection signal obtained when the magnetism is detected.

INDUSTRIAL APPLICABILITY

As explained above, the present invention is useful in detecting and determining plural magnetic materials with mutually different coercive forces by using a small-size magnetic property determination apparatus.

EXPLANATION OF REFERENCE NUMERALS

1 Magnetic property determination apparatus
2 Magnetic detection unit
3 Magnetization unit
10 Magnetic sensor
20, 121, 122 Magnetization magnet
30 Bias magnet
100 Paper sheet
131 to 136 Permeable member

The invention claimed is:

1. A magnetic property determination apparatus that detects a magnetic property of each magnetic material included in a paper sheet transported through a transport path and determines the magnetic materials, the apparatus comprising:
a magnetization unit that generates a magnetization magnetic field including a first magnetic field region and a second magnetic field region on the transport path, a magnetic field intensity and a magnetic field direction are set different between the first magnetic field region and the second magnetic field region so that the magnetic materials are magnetized in different magnetization directions depending on coercive forces of the magnetic materials; and
a magnetic detection unit that generates a bias magnetic field on the transport path downstream of the magnetization unit in a transport direction, and that detects a magnetic charge of the magnetic materials by detecting variations of the bias magnetic field
wherein
the magnetization unit includes a first magnet and a first permeable member arranged on one side of the transport path and a second magnet and a second permeable member arranged on the other side of the transport path,
the first magnetic field region is generated by shifting in the transport direction the first magnet and the second magnet, and
the second magnetic field region is generated by shifting in the transport direction the first magnetically permeable member and the second magnetically permeable member.

2. The magnetic property determination apparatus as claimed in claim 1, wherein the magnetic property determination apparatus determines a type among three types of the magnetic materials, a first magnetic material having a coercive force, a second magnetic material having a coercive force lower than that of the first magnetic material, and a third magnetic material having a coercive force lower than that of the second magnetic material, and
the first magnetic field region, when the transport direction is 0 degree, is set in a range between −100 degrees and −170 degrees, and the magnetic field intensity thereof is set to 1.5 times or more of a coercive force of the first magnetic material.

3. The magnetic property determination apparatus as claimed in claim 2, wherein the second magnetic field region, when the transport direction is 0 degree, is set in a range between 100 degrees and 180 degrees, and the magnetic field intensity thereof is set to 1.5 times or more of the second magnetic material and to 1 time or less of the coercive force of the first magnetic material.

4. The magnetic property determination apparatus as claimed in claim 1, wherein the magnetization unit has, in a surface facing toward the transport path, a first magnetic-pole surface substantially parallel to a transport surface and a second magnetic-pole surface that is distant from the transport surface than the first magnetic-pole surface.

5. The magnetic property determination apparatus as claimed in claim 1, wherein a magnetic field intensity between the first magnetic field region and the second magnetic field region is weaker than the magnetic field intensity of the first magnetic field region but stronger than the magnetic field intensity of the second magnetic field region, and a magnetic field intensity between the second magnetic field region and the bias magnetic field is weaker than the magnetic field intensity of the second magnetic field region.

6. The magnetic property determination apparatus as claimed in claim 5, wherein
the magnetic property determination apparatus determines a type among three types of the magnetic materials, a first magnetic material having a coercive force, a second magnetic material having a coercive force lower than that of the first magnetic material, and a third magnetic material having a coercive force lower than that of the second magnetic material,
the first magnetic field region has a magnetic field intensity that magnetizes the three types of magnetic materials,
the magnetic field intensity between the first magnetic field region and the second magnetic field region is a magnetic field intensity that does not affect a magnetization direction of only the first magnetic material, and
the magnetic field intensity between the second magnetic field region and the bias magnetic field is a magnetic field intensity that does not affect the magnetization direction of the first magnetic material, that affects a magnetization direction of the second magnetic material, and that changes a magnetization direction of the third magnetic material to the magnetic field direction thereof.

7. A magnetic property determination method of detecting a magnetic property of each magnetic material included in a paper sheet transported through a transport path and determining the magnetic materials, the method comprising:
generating a magnetization magnetic field including a first magnetic field region and a second magnetic field region on the transport path, a magnetic field intensity and a magnetic field direction are set different between the first magnetic field region and the second magnetic field region so that the magnetic materials are magnetized in different magnetization directions depending on coercive forces of the magnetic materials; and detecting a magnetic charge of the magnetic materials magnetized by using a magnetic detection unit that generates a bias magnetic field on the transport path downstream in a transport direction of a magnetization position, and that detects the magnetic charge of the magnetic materials by detecting variations of the bias magnetic field wherein the first magnetic field region is generated by shifting in the transport direction a first magnet arranged on one side of the transport path and a second magnet arranged on the other side the transport path, and the second magnetic field region is generated by shifting in the transport direction a first magnetically permeable member arranged on the one side of the transport path and a second magnetically permeable member arranged on the other side the transport path.

\* \* \* \* \*